United States Patent [19]

Schwede et al.

[11] Patent Number: 5,519,027

[45] Date of Patent: May 21, 1996

[54] D-HOMO-(16-ENE)-11β-ARYL-4-ESTRENES, PROCESS FOR THEIR PRODUCTION AS WELL AS THEIR USE AS PHARMACEUTICAL AGENTS

[75] Inventors: Wolfgang Schwede; Eckhard Ottow; Arwed Cleve; Walter Elger; Krzysztof Chwalisz; Martin Schneider, all of Berlin, Germany

[73] Assignee: Schering Aktiengesellschaft, Berlin, Germany

[21] Appl. No.: 78,326

[22] PCT Filed: Dec. 21, 1991

[86] PCT No.: PCT/EP91/02495

§ 371 Date: Feb. 25, 1994

§ 102(e) Date: Feb. 25, 1994

[87] PCT Pub. No.: WO92/11279

PCT Pub. Date: Jul. 9, 1992

[30] Foreign Application Priority Data

Dec. 22, 1990 [DE] Germany ............ 40 42 005.1

[51] Int. Cl.⁶ ............ C07J 63/00; A61K 31/565; A61K 31/58
[52] U.S. Cl. ............ 514/277; 514/680; 546/285; 568/326
[58] Field of Search ............ 546/285, 326; 514/277, 680

[56] References Cited

U.S. PATENT DOCUMENTS

| | | | |
|---|---|---|---|
| 4,536,401 | 8/1985 | Neef et al. | 514/173 |
| 4,609,651 | 9/1986 | Rohde et al. | 514/179 |

FOREIGN PATENT DOCUMENTS

| | | |
|---|---|---|
| 0116974 | 8/1984 | European Pat. Off. |
| 0127864 | 12/1984 | European Pat. Off. |
| 0147361 | 7/1985 | European Pat. Off. |

OTHER PUBLICATIONS

CA 120: 323998 (Abstract of Chinese patent CN 92–101450 Jan. 31, 1992) Faming.
CA 115: 114882 (Abstract of East German patent DD 289542 May 2 1991) Kasch, et al.

*Primary Examiner*—Gary Geist
*Assistant Examiner*—Catherine Scalzo
*Attorney, Agent, or Firm*—Millen, White, Zelano & Branigan

[57] ABSTRACT

New D-homo-(16-ene)-11β-aryl-4-estrenes of general formula I

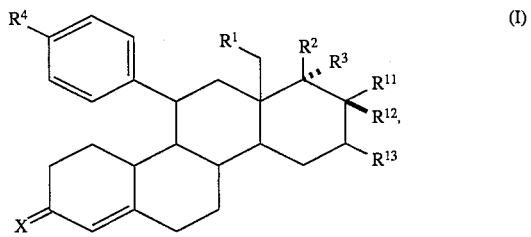

as well as their pharmaceutically compatible addition salts with acids are described in which X stands for an oxygen atom, the hydroxyimino grouping >N–OH or two hydrogen atoms, $R^1$ stands for a hydrogen atom or a methyl group, $R^2$ stands for an hydroxy group, a $C_1$–$C_{10}$ alkoxy or $C_1$–$C_{10}$ acyloxy group, $R^{11}$ stands for a fluorine, chlorine or bromine atom, and then $R^{12}$ and $R^{13}$ together mean an additional bond or $R^{11}$ stands for a straight-chain or branched-chain $C_1$–$C_4$-alkyl radical or a hydrogen atom, and then $R^{12}$ and $R^{13}$ each mean a hydrogen atom or together mean an additional bond, and $R^3$ and $R^4$ have the usual meanings indicated in the description for competitive progesterone antagonists.

The invention further relates to a process for the production of new compounds, pharmaceutical preparations containing these compounds, their use for the production of pharmaceutical agents as well as the new intermediate products necessary for the process.

The new compounds have a strong affinity to the gestagen receptor and show strong antigestagen as well as antiglucocorticoid, antimineral corticoid and antiandrogenic properties.

7 Claims, No Drawings

D-HOMO-(16-ENE)-11β-ARYL-4-ESTRENES, PROCESS FOR THEIR PRODUCTION AS WELL AS THEIR USE AS PHARMACEUTICAL AGENTS

This application is a 371 of PCT/EP91/02495 filed Dec. 21, 1991, published as WO/92/11279.

This invention relates to compounds of general formula I

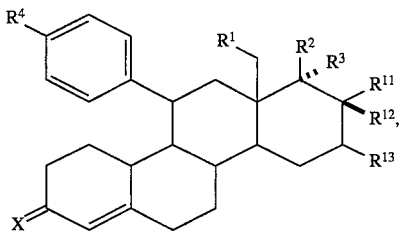  (I)

in which

X stands for an oxygen atom, the hydroxyimino grouping >N—OH or two hydrogen atoms, $R^1$ stands for a hydrogen atom or a methyl group, $R^2$ stands for an hydroxy group, a $C_1$–$C_{10}$ alkoxy or $C_1$–$C_{10}$ acyloxy group, $R^3$ stands for a hydrogen atom, the grouping —$(CH_2)_n CH_2 Z$, in which n is 0, 1, 2, 3, 4 or 5, Z means a hydrogen atom, the cyano group or the radical —$OR^5$ with $R^5$=H, $C_1$–$C_{10}$ alkyl or $C_1$–$C_{10}$ acyl, the grouping —$(CH_2)_m C\equiv C—Y$, in which m means 0, 1 or 2 and Y means a hydrogen, fluorine, chlorine, bromine or iodine atom, a methyl, $C_1$–$C_{10}$ hydroxy alkyl, methyl, $C_1$–$C_{10}$ alkoxyalkyl, methyl, $C_1$–$C_{10}$ acyloxyalkyl radical, the grouping —$(CH_2)_p$—CH=CH—$(CH_2)_k CH_2 R^6$, in which p means 0 or 1 and k means 0, 1 or 2 and $R^6$ means a hydrogen atom, a hydroxy group, a $C_1$–$C_4$ alkoxy or $C_1$–$C_4$ acyloxy radical, or else $R^2$ and $R^3$ together stand for a radical of the formula

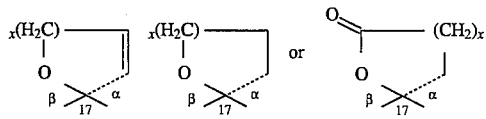

in which x=1 or 2

$R^4$ stands for a hydrogen atom, a cyano group, a chlorine, fluorine, bromine, iodine atom, for a trialkylsilyl group, trialkylstannyl group, for a straight-chain or branched, saturated or unsaturated $C_1$–$C_8$ alkyl, $C_1$–$C_8$ acyl or alkoxyalkyl radical, for an amino group

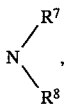

in which $R^7$ and $R^8$, independently of one another, mean a hydrogen atom or a $C_1$–$C_4$ alkyl group, or for a corresponding amine oxide

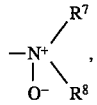

or stands for the groupings —$OR^9$ or —$S(O)_i R^9$ with i=0, 1 or 2, in which $R^9$ means a hydrogen atom, a methyl, ethyl, propyl, isopropyl, methoxyphenyl, allyl or a 2-dimethylaminoethyl group, or for a heteroaryl radical of the formula Iα

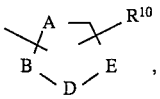  (Iα)

in which A symbolizes a nitrogen, oxygen or sulfur atom, —B—D—E— the element sequence —C—C—C—, —N—C—C— or —C—N—C— and $R^{10}$ a hydrogen atom, a cyano group, a chlorine, fluorine, bromine or iodine atom, a trialkylsilyl, trialkylstannyl group, a straight-chain or branched, saturated or unsaturated $C_1$–$C_8$-alkyl, $C_1$–$C_8$-acyl or alkoxyalkyl radical, for an amino group

in which $R^7$ and $R^8$ independently of one another, mean a hydrogen atom or a $C_1$–$C_4$ alkyl group, or a corresponding amine oxide

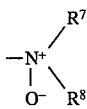

or the grouping —$OR^9$ or —$S(O)_i R^9$ with i=0, 1 or 2, in which $R^9$ means a hydrogen atom, a methyl, ethyl, propyl, isopropyl, methoxyphenyl, allyl or a 2-dimethylaminoethyl group, or for a heteroaryl radical of formula Iβ

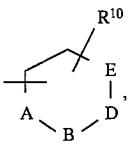  (Iβ)

in which A means a nitrogen atom and —B—D—E— means the element sequence —C—C—C—, —N—C—C—, —C—N—C— or —C—C—N— and R has the meaning already indicated, or for a phenyl radical of formula Iγ

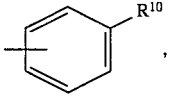  (Iγ)

in which $R^{10}$ has the meaning already indicated, $R^{11}$ stands for a fluorine, chlorine or bromine atom, and then $R^{12}$ and $R^{13}$ together mean an additional bond or $R^{11}$ stands for a straight-chain or branched-chain $C_1$–$C_4$-alkyl radical or a hydrogen atom, and then $R^{12}$ and $R^{13}$ each mean a hydrogen atom or together mean an additional bond, as well as their pharmacologically compatible addition salts with acids, process for their production, pharmaceutical preparations containing these compounds, their use for the production of pharmaceutical agents as well as the new intermediate products necessary for this purpose.

The invention relates especially to compounds, in which X stands for an oxygen atom.

The alkoxy, acyloxy, alkyl, acyl as well as hydroxyalkyl groups contained in $R^2$, $R^3$, $R^5$ and Y of general formula I each are to contain 1 to 10 carbon atoms and the alkoxyalkyl or acyloxyalkyl groups in Y, 2 to 10 carbon atoms. In this case, the methoxy, ethoxy, propoxy and isopropoxy group can be named as preferred groups of the alkoxy groups, the formyl(oxy), acetyl(oxy) and propionyl(oxy) groups from the acyl(oxy) groups are especially important.

In the alkyl groups above all methyl, ethyl, propyl, isopropyl as well as tert-butyl groups can be mentioned and of the hydroxyalkyl groups the corresponding radicals substituted in any position with a hydroxy group are preferred.

0, 1, 2 and 3 are especially suitable for n; if Z=CN, a cyanomethyl group (n=0) is especially preferred. In addition to the groups already mentioned, Y can preferably be a hydrogen, chlorine or bromine atom.

Of the alkenyl radicals in $R^3$ the propenyl and butenyl groups, which can be present in the E or Z configuration, are preferred i e., if $R^3$ stands for —$(CH_2)_p$—CH=CH—$(CH_2)_k$—CH—$R^6$, k preferably is to be 0 or 1 and p=0.

Among the alkoxy or acyloxy groups mentioned for $R^6$, which can be both straight-chain and branched, methoxy, ethoxy, propoxy, isopropoxy or the formyloxy, acetyloxy and propionyloxy groups are especially preferred.

Of the $C_1$–$C_8$ alkyl and alkoxyalkyl radicals, which can stand for $R^4$, these above all are the methyl, ethyl, propyl, isopropyl, cyclopentyl and cyclohexyl radical or the alkoxy methyl and 1- or 2-alkoxyethyl groups with said alkyl radicals; by the $C_1$–$C_8$ acyl radicals for $R^4$ especially acetyl, propionyl and isobutyryl radicals are meant.

If $R^4$ stands for the amino group

$R^7$ and $R^8$ preferably each mean a methyl radical, but the ethyl radical also has special importance, and then either both radicals on the nitrogen atom stand for an ethyl radical or one stands for a methyl radical and the other for an ethyl radical. For the substituent $R^9$ the methyl, ethyl and 2-(dimethylamino)ethyl groups are especially to be emphasized.

Of the heteroaryl radicals possible according to formula Iα, the 3-thienyl, 3-furyl and 3-pyrrolyl radicals are preferred with $R^{10}$ meaning a cyano, methoxy or dimethylamino group.

As heteroaryl radicals of formula Iβ, according to the invention especially 3- or 4-pyridyl, 5-pyrimidinyl, 4-pyridazinyl or pyrazinyl radicals are suitable.

The phenyl radical of formula Iγ exhibits as substituent $R^{10}$ especially the cyano, methoxy or dimethylamino group, and again these substituents preferably are in the p-position of the phenyl ring.

Compounds named below are especially preferred according to the invention:

11β-Aryl-D-homo-4,9-estradien- and 4,9,16-estratrien-3-one with a 17β-hydroxy and 17α-(3-hydroxypropyl) group, with a 17-spironolactone group, with an oxathiolane-S-oxide-, oxazolidine- or oxathiazolidine-S-oxide ring (with inclusion of the 17 carbon atom) follow from EP-A 0 116 974, 11β-aryl-D-homo-4,9,16-estratrien- 3-one with 17β-hydroxy and a 17α-ethinyl-, -chloroethinyl- or -propinyl substituent follow from EP-A 0 127 864 as well as 11β-aryl-D-homo-4,9,estradien- and 4,9,16-estratrien- 3-one with 17β-hydroxy- and 17α-(3-hydroxyprop-1(Z)enyl)- or 17α-(3-acyloxyprop-1(Z)enyl)-substituents follow from EP-A 0147 361. The known compounds are all described as those with anti-gestagen effectiveness.

17aβ-Hydroxy-11β-(4-methoxyphenyl)-17aα-(1-propinyl)-17a-homoestra- 4,16-dien-3-one 17aβ-hydroxy-11β-(4-methoxyphenyl)-17aα-methyl-17a-homoestra- 4,16-dien-3-one 11β-[4-(3-furanyl)phenyl]-17aα-hydroxy-17aα-(1-propinyl)- 17a-homoestra-4,16-dien-3-one 11β-(4-acetylphenyl)-17aβ-hydroxy-17aα-(1-propinyl)-17a-homoestra- 4,16-dien-3-one 17aβ-hydroxy-17aα-(3-hydroxypropyl)-11β-[4-(3-pyridinyl)phenyl] -17a-homoestra-4,16-dien-3-one (Z)-4'-[17aβ-hydroxy-17aα-(3-hydroxy-1-propenyl)-3-oxo-17a-homo- 4,16-dien-11β-yl]-[1,1'-biphenyl]-4-carbonitrile 11β-[4-(3-furanyl)phenyl]-17aβ-hydroxy-17aα-methyl-17a-homoestra- 4,16-dien-3-one 11β-(4-acetylphenyl)-17aβ-hydroxy-17aα-(3-hydroxypropyl)- 17a-homoestra-4-en-3-one 11β-(4-acetylphenyl)-4',5'-dihydrospiro[17a-homoestra-4-ene- 17aβ,2'(3H)-furan]-3-one (Z)-4'-[17aβ-hydroxy-17aα-(3-hydroxy-1-propenyl)-3-oxo-17a-homoestr- 4-en-11β-yl]-[1,1'-biphenyl]-4-carbonitrile 17-chloro-11β-(4-methoxyphenyl)-17aβ-hydroxy-17aα-(1-propinyl)- 17a-homoestra-4,16-dien-3-one 17-chloro-17aβ-hydroxy-17aα-(1-propinyl)-11β-[4-(3-pyridinyl)phenyl] -17a-homoestra-4,16-dien-3-one 11β-(4-acetylphenyl)-17-chloro-17aβ-hydroxy-17aα-(1-propinyl)- 17a-homoestra-4,16-dien-3-one 17-chloro-11β-[4-(3-furanyl)phenyl]17aβ-hydroxy-17aα-(1-propinyl)- 17a-homoestra-4,16-dien-3-one 17-chloro-11β-[4-(3-furanyl)phenyl]-17aβ-hydroxy-17aα-methyl- 17a-homoestra-4,16-dien-3-one 4'-[17-chloro-17aβ-hydroxy-17aβ-methyl-3-oxo-17a-homoestra- 4,16-dien-11β-yl][1,1'-biphenyl]4-carbonitrile (Z)-11β-(4-acetylphenyl)-17-chloro-17aβ-hydroxy-17aα-(3-hydroxy- 1-propenyl)-17a-homoestra-4,16-dien-3-one 11β-(4-acetylphenyl)-17-chloro-17aβ-hydroxy-17aα-(3-hydroxypropyl)- 17a-homoestra-4,16-dien-3-one 17-chloro-11β-[4-(3-furanyl)phenyl]-17aβ-hydroxy-3-oxo-17a-homoestra- 4,16-dien-17aα-acetonitrile 11β-(4-acetylphenyl)-17-fluoro-17aβ-hydroxy-17aα-methyl-17a-homoestra- 4,16-dien-3-one 11β-(4-acetylphenyl)-17-fluoro-17aβ-hydroxy-17aα-(3-hydroxypropyl)- 17a-homoestra-4,16-dien-3-one 11β-(4-acetylphenyl)-17-fluoro-17aβ-hydroxy-17aα-(1-propinyl)- 17a-homoestra-4,16-dien-3-one 17aα-hydroxy-11β-(4-methoxyphenyl)-17aα-(1-propinyl)-17a-homoestr- 4-en-3-one.

The production of the compounds according to the invention takes place according to the reaction pattern below:

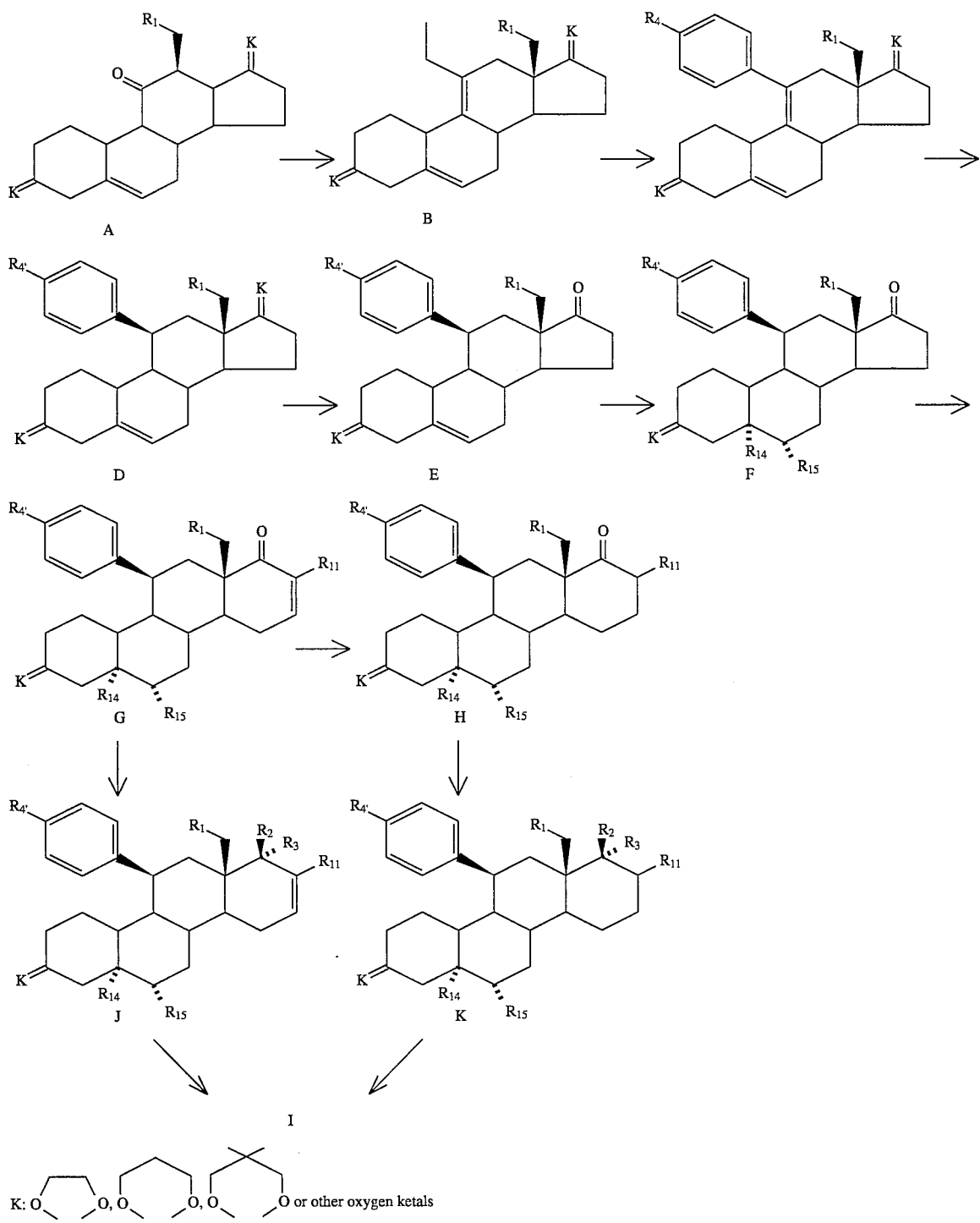

K: $O\diagup\diagdown O$, $O\diagup\diagdown\diagdown O$, $O\diagup\diagdown\diagdown O$ or other oxygen ketals According to this invention compound A (Recl. Trav. Chim. Bays-Pas 107, 331, (1988)) is first converted into a compound of formula B and L stands for a perfluoroalkyl-sulfonyloxy group $C_nF_{2n+1}SO_2O$— (n=1, 2, 3, 4).

Compound B is reacted in the presence of a catalytic amount of a transition metal catalyst with an aryl compound of general formula Z

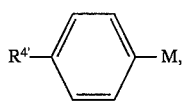

(Z)

in which M stands for one of the radicals

- —B(alkyl)₂
- —Sn(alkyl)₃    alkyl = $C_1$–$C_4$-alkyl radical
- —B(OH)₂
- —ZnHal
- —MgHal    Hal = Cl, Br, I and $R^{4'}$ stands for one of the radicals mentioned under $R_4$ to a compound of general formula C in which $R^1$ has the meaning indicated in formula I and $R^{4'}$ has the meaning indicated in formula Z and optionally, if $R^4$ in formula I is to have a meaning other than $R^{4'}$ in formula C, a compound of general formula C, in which $R^{4'}$ stands for a bromine atom or, after conversion of a methoxy group standing for $R^{4'}$ in a perfluoroalkylsulfonyl group $C_nF_{2n+1}SO_2O$— (n=1, 2, 3, 4) with a compound of general formula VI $$R^4—M \quad (VI),$$

in which $R^4$ has the meaning finally desired for this substituent in formula I and M has the meaning already indicated above in formula Z.

Preferably the trifluoromethylsulfonyloxy group stands for L in compound B. As transition metal catalyst for coupling of the aryl compound of general formula Z with the compounds having the leaving group L, palladiumtetrakistriphenylphosphine (see the literature indicated below) are used according to the examples of this invention; but nickeltetrakistriphenylphosphine or similar transition metal catalysts could be used just as well.

The variant, that the finally desired substituent $R^4$ is introduced by the functionalization of a bromine or methoxy substituent $R^{4'}$ in compound C, is to be selected if the aryl compound of general formula Z to be coupled, in which $R^{4'}$ is already identical with $R^4$, is not available or is not suitable for coupling. Transition-metal-catalyzed aryl coupling reactions of compounds of the type of general formula X with compounds, that have a leaving group, are described, for example, in: with —Sn(alkyl)₃-substituted aromatic compounds: J. E. McMurry and S. Mohanraj, Tetrahedron Letters, 24, No. 27, pp. 2723–2726, 1983; X. Lu and J. Zhu, Communications, pp. 726–727, 1987; Q.-Y. Chen and Z.-Y. Yang, Tetrahedron Letters 27, No. 10, pp. 1171–1174, 1986; S. Cacchi, P. G. Ciattini, E. Morera and G. Ortar, Tetrahedron Letters, 27, No. 33, pp. 3931–3934, 1986; E. M. Echavarren and J. K. Stille, J. Am. Chem. Soc. 1987, 109, pp. 5478–5486 and J. Am. Chem. Soc. 1988, 110, p. 1557; with —B(OH)₂ and —B(Oalkyl)₂-substituted aromatic compounds: Y. Hoshino, N. Miyaura and A. Suzuki, Bull. Chem. Soc. Jpn. 61, 3008 (1988); H. Matsubasa, K. Seto, T. Tahara and S. Takahashi; Bull. Chem. Soc. Jpn. 62, 3896 (1989); with -ZnCl-substituted aromatic compounds: R. McCague, Tet. Lett., 28, 701 (1987); A. Arcadi, A. Burini, S. Cacchi, M. Delmastro, F. Marinelli, B. Pietroni, Syn. Les., 1, 1980, p. 47.

The compounds of general formula D, that are suitable as initial products for the production of 10β-H-steroids of general formula I, are easy to produce, by a compound of formula C, in which $R^{4'}$ and $R^1$ have the meaning mentioned in the formulas, without destruction of the aromatic system and the 5,6-double bond being reduced to a compound of general formula D, in which $R^4$ and $R^1$ have the already mentioned meaning.

11β-Aryl compound D (stereoseletive reduction) is formed in the reduction of C.

For reduction of the 9(11)-double bond in C various methods according to the invention can be used:

According to the invention the reduction with an electropositive metal in an electron solvating solvent or in an solvent containing a solutizer is preferred. Ammonia is suitable in the first place as electron-solvating solvent.

For the reduction equimolar amounts of reducing agent are already sufficient, however, a considerable excess of reducing agent can also be used, without the aromatic system and/or the 5,6-double bond being attacked.

As electropositive metals, all metals suitable for a Birch reduction are usable. According to the invention, lithium, potassium, sodium and calcium—and of these especially lithium—are preferred.

Selective cleavage of the keto protective group in 17 position with a weak acid (acetic acid, oxalic acid) yields compound E.

The compounds of formula E are epoxidized, for example, by using organic peracid or with hydrogen peroxide in the presence of hexachloroacetone or nitrotrifluoroacetophenone. The following reactions are performed either in the presence of epoxide or, by reductive opening by using complex hydrides to compounds of type F with $R^{14}$=OH and $R^{15}$=H. Then there are available by reaction of the enol compounds of the 17-ketones F, for example, of trialkylsilylenol ether with CXY type carbons, in which X=Y=Cl; X=Y=Br; X=F, Y=Cl, Y=methyl or X=Cl, can be Y=H, or by Simmons Smith reaction with subsequent opening of the 3-ring adducts, compounds of general formula G with $R_{11}$= F, Cl, Br, methyl or hydrogen. The corresponding carbenes CXY can be produced, for example, from $CH_3CH_2XY$ $CHX_2Y$ or $CH_2XY$ by processing with bases, such as potassium tertiarybutanolate or from the sodium salt of trichloroacetic acid or the tribromoacetic acid by heating in suitable solvents, such as, for example, dimethoxyethane/ tetrachloroethylene or from the esters of trichloroacetic acid or tribromoacetic acid, for example, by reaction with sodium methanolate. Optionally also compounds of type H can also be produced from G by hydrogenation or reaction with trialkyl tin hydrides, and $R^{11}$ stands for methyl or hydrogen here. The 17-chlorine compounds can also be converted later by reduction with lithium aluminum hydride or Birch reaction into the corresponding 17-unsubstituted compounds.

Alternatively, for this purpose, the ring enlargement can also take place by a Tifenau-Demjenov rearrangement, starting from the compounds of type F, and in this case H is directly obtained.

The compounds of general formulas G and H can now be converted into compounds of general formula I.

To this end, substituents $R^2$ and $R^3$ desired on the 17a-C atom are first introduced. This introduction takes place analogously to processes known in the literature (for example, J. Fried, J. A. Edwards, "Organic Reactions in Steroid Chemistry," Van Nostrand Reinhold Company, 1972, Vol. 1 and 2; "Terpenoids and Steroids," Specialist Periodical Report, The Chemical Society, London, Vol. 1–2) by nucleophilic addition on the C 17a ketone.

The introduction of the substituent —C≡C—Y as $R^3$, in which Y has the meaning indicated above, takes place with the help of a metallized compound of general formula MC≡C—Y', in which Y' is an alkine protecting group, such as, for example, trimethylsilyl or tert-butyldimethylsilyl.

The organometallic compound can also be formed in situ and reacted with the 17 ketone. Thus, for example, it is possible to cause acetylene and an alkali metal, especially potassium, sodium or lithium, in the presence of an alcohol or in the presence of ammonia, to act on the 17 ketone in a suitable solvent. The alkali metal can also be effective in the form, for example, of methyllithium or butyllithium. Especially dialkyl ether, tetrahydrofuran, dioxane, benzene and toluene are suitable as solvents.

The introduction of 3-hydroxypropine, 3-hydroxypropene in 17a position takes place by reaction of the 17a-ketone with the dianion of propargyl alcohol (3-hydroxypropine), for example, with the dipotassium salt of the propargyl alcohol, generated in situ, to the 17aα-(3-hydroxyprop-1-inyl)-17β-hydroxy derivative or with metallized derivatives of the 3-hydroxypropine, for example, with 1-lithium-3-(tetrahydropyran-2'-yloxy)-prop-1-in-1-ide, to the 17a-[3-(tetrahydropyran-2'-yloxy)-prop-1-inyl]-17aβ-hydroxy derivative, which then can be hydrogenated to the 17a-(3-hydroxypropyl or hydroxypropenyl)17aβ-hydroxy compounds. This comes about, for example, by hydrogenation at room temperature and normal pressure in solvents such as methanol, ethanol, propanol, tetrahydrofuran (THF) or ethyl acetate with addition of noble metal catalysts such as platinum or palladium.

The introduction of homologous hydroxyalkine, hydroxyalkene and hydroxyalkane groups takes place in a corresponding way with homologs of the propargyl alcohol.

The compound with the Z-configured double bond in the hydroxypropenyl group results by hydrogenation of the acetylenic triple bond with a deactivated noble metal catalyst (J. Fried, J. A. Edwards: Organic Reactions in Steroid Chemistry. Van Nostrand Reinhold Company 1972, page 134; and H. O. House: Modern Synthetic Reactions 1972, p. 19). Suitable as deactivated noble metal catalysts are, for example, 10% palladium on barium sulfate in the presence of an amine or 5% palladium on calcium carbonate with addition of lead(II) acetate. The hydrogenation is interrupted after the absorption of an equivalent of hydrogen.

The compound with the E-configured double bond in the hydroxypropenyl group results by reduction of the acetylenic triple bond in a way known in the art. In the literature a whole series of methods are described for the conversion of alkines into transolefins, for example, the reduction with sodium in liquid ammonia (J. Am. Chem. Soc. 63 (1941) 216) with sodium amide in liquid ammonia (J. Chem. Soc. 1955, 3558), with lithium in low-molecular amines (J. A. Chem. Soc. 77 (1955) 3378) with boranes (J. Am. Chem. Soc. 93 (1971) 3395 and 94 (1972) 6560), with diisobutylaluminum hydride and methyllithium (J. Am. Chem. Soc. 89 (1967) 5085) and especially with lithium aluminum hydride/alcoholate (J. Am. Chem. Soc. 89 (1967) 4245). Another possibility is the reduction of the triple bond with chromium(II) sulfate in the presence of water or dimethylformamide in weakly acidic medium (J. Amer. Chem. Soc. 86 (1964) 4358) as well as generally the reduction by the action of transition metal compounds with changing of the oxidation stage.

The introduction of the hydroxalkenes can also take place directly by addition of a corresponding metallized hydroxyalkenyl compound, such as, for example, 1-lithium-3-(tetrahydropyran-2'-yloxy)-prop-1(E)-ene (J. Org. Chem.40 2265) or 1-lithium-3-(tetrahydropyran- 2'-yloxy)-prop-1(Z)-ene (Synthesis 1981, 999). Homologs can also be introduced in this way.

The introduction of 3-hydroxypropane in 17a position can also take place directly by reaction of the 17a-ketone with metallized derivatives of 3-halopropanols—and the hydroxy group in the metallizing step is present as alcoholate (Tetrahedron Letters 1978, 3013) or as protected function (J. Org. Chem. 37, 1947)—to the 17-(3-hydroxypropyl)-17β-hydroxy compound or to the compound protected on the terminal hydroxy group. For example, ethoxyethyl, tetrahydropyranyl and methoxymethyl groups are suitable as protecting groups.

If end products of formula I are desired with $R^2/R^3$ meaning

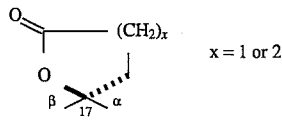

$x = 1$ or $2$ thus the 17a-(3-hydroxypropyl) or 17a-(4-hydroxybutyl) compound is oxidized in a way known in the art, for example with Jones reagent, manganese oxide, pyridinium dichromate, pyridinium chlorochromate, chromic acid pyridine or the Fetizon reagent silver carbonate/Celite (Comp. rend. 267 [1968] 900).

The preparation of end products of formula I with $R^{2'}/R^3$ meaning

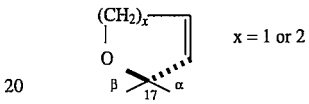

$x = 1$ or $2$ takes place by cyclization reaction of the corresponding 17a-(3-hydroxyprop- 1-(Z)-enyl or 17a-(4-hydroxybut-1-(Z)-enyl-17a-β-hydroxy feedstock. Hydrogenation of the unsaturated 5- or 6-ring spiroether on the palladium/activated carbon catalyst leads to the saturated spiroether.

The synthesis of the 17a-cyanomethyl side chain takes place in a way known in the art from the 17a-ketone, for example, by the 17a-spiroepoxide and cleavage of the spiroepoxide with HCN according to Z. Chem. 18 (1978) 259–260.

Also the introduction of the 17a-hydroxyacetyl side chain takes place according to methods known in the art, for example, according to the methods described in J. Org. Chem. 47 (1982), 2993–2995, Chem. Ber. 113 (1984), 1184 or U.S. Pat. No. 4,600,538.

Free hydroxy groups can be akylated or acylated in a way known in the art.

The next reaction step serves the synthesis of substituents $R^4$ or $R^{4'}$ in the p-position on the 11β-phenyl ring.

This procedure is necessary, if $R^4$ is not directly introduced when compound B is coupled with aryl compound Z to compound C. Basically this reaction step can be performed at every stage of the process, even after cleavage of the protective group(s).

As starting point for this synthesis, a compound is used, in which $R^4$=OH, that can be obtained from the corresponding methoxy compound by ether cleavage, for example, with sodium ethane thiolate in a solvent such as dimethylformamide.

By reaction of the hydroxy compound with a perfluoro-$(C_1-C_4)$-alkyl sulfonic acid anhydride or halide in the presence of a base such as pyridine or 4-(dimethylamino)-pyridine, the corresponding 11β-[4-(perfluoroalkyl sulfonyloxy)-phenyl] compound is obtained (P. J. Stang, M. Hanack and L. R. Subramanian, Synthesis 85, (1982)). The perfluoroalkysulfonate formation can even take place at an earlier stage.

In the subsequent coupling of the 11β-aryl compound with $R^{4''}$—Sn(alkyl)3 or $R^{4''}$—$BL_2$ the procedure is such that either in a transition-metal-catalyzed reaction (preferably Pd°) the perfluoroalkyl sulfonate leaving group is displaced under basically almost simultaneous substitution by the desired substituent or its precursor (aryl couplings with tin compounds: by the desired substituent or its precursor (J. E. McMurry and S. Mohanraj, Tetrahedron Letters, 24, No. 27, pp. 2723–2726, 1983; X. Lu and J. Zhu, Communications, pp. 726–727, 1987; Q.-Y. Chen and Z.-Y. Yang, Tetrahedron Letters 27, No. 10, pp. 1171–1174, 1986; S. Cacchi, P. G. Ciattini, E. Morera and G. Ortar, Tetrahedron Letters, 27, No. 33, pp. 3931–3934, 1986; E. M. Echavarren and J. K. Stille, J. Am. Chem. Soc. 1987, 109, pp. 5478–5486); with boron compounds: Synthesis 936 (1984), Chem. Pharm. Bull. 33, 4755–4763 (1985); J.Org. Chem. 49, 5237–5243 (1984); Bull. Chem. Soc. Jpn. 61, 3008–30108 (1988); or a corresponding triorganylstannyl, preferably tri-n-alkylstannyl compound, intermediately and transition-metal-catalyzed, is produced from the perfluoroalkyl sulfonate compound [J. K. Stille, Angew. Chem. 98 (1986), pp. 504–519]. It is then reacted in a one-pot reaction with a halogen, preferably, bromine and iodine substituted carbocyclic or heterocyclic aromatic compound [Y. Yamamoto, Y. Azuma, H. Mitoh, Communications, pp. 564–565, 1986; T. J. Bailey, Tetrahedron Letters, 27, No. 37, pp. 4407–4410, 1986], which optionally can also carry additional substituents; the 11β-phenyl radical then exhibits in it the desired, or a precursor of the desired substitution.

Numerous such reactions with steroids, in which a trifluoromethane sulfonate group is in 4 position of an 11β-phenyl ring, are described in EP-A-0283428.

Free hydroxy groups can be alkylated or acylated in a way known in the art.

Dialkylamines can be converted by suitable oxidizing agents (e.g., hydrogen peroxide or peracids) into the desired N oxides [see, e.g., Kontakte (Darmstadt), 1986, 3, p. 12].

Compounds with a dialkylamine substituent on the 11β-phenyl ring by reaction with cyanogen bromide in aprotic solvents such as, for example, dioxane, benzene or toluene at elevated temperature (amine decomposition according to Braun) analogously to instructions indicated for the example in Org. Reactions 7, 198 (1935), K. W. Bentley, Techniques of Organic Chemistry 11, 773 (1963) and Houben-Weyl, 5/4, 151 (1960) can be converted in good yield into the corresponding (N-cyano-N-alkylaminoaryl) derivatives.

Depending on the finally desired meaning of

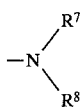

in the end product these derivatives in a way known in the art are reduced to the corresponding dialkylamine compounds (for example, with diisobutylaluminium hydride in toluene to the N-formyl-N-alkylaminophenyl intermediate products and then with lithium aluminum hydride) or N—H—N alkyl compounds (for example, with lithium aluminum hydride or with lithium in liquid ammonia). The latter are then optionally acylated in a way known in the literature and optionally then are reduced in a known way, e.g. with lithium aluminum hydride to the new dialkylamine derivative (see DE 36 23 038).

Optionally substituent $R^4$ can be synthesized first and then the introduction of substituents $R^2$ and $R^3$ can be performed depending on whether the process conditions of the second reaction step adversely affect the first introduced or synthesized substituents.

Still present protecting groups are cleaved according to usual methods.

The resulting compounds of general formula I with X meaning an oxygen atom, by reaction with hydroxylamino hydrochloride in the presence of tertiary amines at temperatures between −20° and −40° C., optionally can be converted into the oximes (formula I with X meaning the hydroxyimino grouping >N–OH, and the hydroxy group can be in syn- or anti-position). Suitable tertiary bases are, for example, trimethylamine, triethylamine, pyridine, N,N-dimethylaminopyridine, 1,5-diazabicyclo[4.3.0]non-5-ene (DBN) and 1,8-diazabicyclo[5.4.0]undec-7-ene (DBU), and pyridine is preferred.

Removal of the 3-oxo group to an end product of general formula I with X meaning 2 hydrogen atoms can take place, e.g., according to the instructions indicated in DE-A-2805490 by reductive cleavage of the thioketal.

The new compounds of general formula I as well as their addition salts with pharmaceutically compatible acids are valuable pharmaceutical agents. Thus they have a strong affinity for the gestagen receptor and have surprisingly strong antigestagen as well as antiglucocorticoid, antimineralcorticoid and antiandrogen properties. These important biological availabilities can be used for medicinal proposes.

Active ingredients of this type with marked antigestagen activity are suitable for inducing abortions, since they displace progesterone from the receptor necessary for maintaining the pregnancy. Therefore they are valuable and of interest in regard to their use for postcoital fertility control.

Moreover, the new compounds can be used for treatment of endometriosis. They can also be used against hormonal irregularities, for inducing menstruation and for inducing labor. Further, they can be used for treatment of hormone-dependent carcinomas.

The compounds according to the invention of general formula I as well as their addition salts with pharmaceutically compatible acids also exhibit an antiglucocorticoid activity and thus can be used also as pharmaceutical agents for the treatment of corticoid-induced disorders (glaucoma) as well as for combatting of side effects, which occur in the long-term treatment with glucocorticoids (Cushing's syndrome). Therefore they make it also possible to combat disorders attributable to hypersecretion of the glucocorticoids, especially obesity, arteriosclerosis, hypertension, osteoporosis, diabetes as well as insomnia.

The compounds according to the invention of general formula I as well as their addition salts with pharmaceutically compatible acids with antiandrogenic activity can be used in the treatment of hypertrophy and prostate cancer. Further, they make possible a specific treatment of androgenizing phenomena in women: pathological hairiness in hirsutism, androgenic alopecia as well as increased sebaceous gland function in the case of acne and seborrhea can be favorably influenced.

The invention thus relates also to pharmaceutical agents based on the compounds of general formula I as well as their addition salts with pharmaceutically compatible acids, optionally together with the usual auxiliary agents and vehicles.

The compounds according to the invention and their salts can be processed according to methods of Galenicpharmacy known in the art into pharmaceutical preparations for enteral, percutaneous, parenteral or local administration. They can be administered in the form of tablets, coated tablets, gel capsules, granular powders, suppositories, implants, injectable sterile aqueous or oily solutions, suspensions or emulsions, ointments, creams and gels.

The active ingredient or ingredients in this case can be mixed with the auxiliary agents usual in galenicals such as, for example, gum arabic, talc, starch, mannitol, methylcellulose, lactose, surfactants such as Tween® or Myrj®, magnesium stearate, aqueous or nonaqueous vehicles, paraffin derivatives, wetting, dispersing, emulsifying agents, preservatives and aromatic substances for taste correction (e.g., essential oils).

The invention thus relates also to pharmaceutical compositions, which contain as active ingredient at least one compound according to the invention or one of its addition salts with pharmaceutically compatible acids. As addition salts of the products according to the invention with acids hydrochlorides and methane sulfonates can be especially mentioned. A dosage unit contains about 1–100 mg of active ingredient(s).

The dosage of the compounds according to the invention for humans is about 1–1000 mg per day.

Pharmacological tests:

The strong affinity to the gestagen receptor follows from the known gestagen receptor binding test described, i.a., in EP-A 0 190 759. The following compounds were tested:

17-chloro-11β-(4-methoxyphenyl)-17aβ-hydroxy-17aα-(1-propinyl)- 17a-homoestra-4,16,dien-3-one (A)

17-chloro-17aβ-hydroxy-17aα-(1-propinyl)-11β-[4-(3-pyridinyl)phenyl- 17a-homoestra-4,16,dien-3-one (B)

17-chloro-11β-[4-(3-furanyl)phenyl]-17aβ-hydroxy-17aα-methyl- 17a-homoestra-4,16,dien-3-one (C)

The test compounds have the following competition factors (reference substance: 3H-progesterone: tissue from rabbit uterus).

| Test compound | A | B | C |
| --- | --- | --- | --- |
| Competition factor K | 1.5 | 3.5 | 4.5 |

For characterization of the antigestagen effects the abortive effect on pregnant rats was determined according to the test described in EP-A-0 283 428.

Compounds A, B and C (see table 1) were studied.

Administration of the test compounds on d5–d7 p.c.p.o.; autopsy on d9 p.c.

The following examples explain the invention in greater detail:

EXAMPLE 1

Production of 17-chloro-11β-(4-methoxyphenyl)-17aβ-hydroxy- 17aα-(1-propinyl)-17a-homoestra-4,16-dien-3-one A) 3,3;17,17-Bis[1,2-ethanediylbis(oxy)]-11-[ [(trifluoromethyl)sulfonyl]oxy]estra-5,9(11)-diene (1A)

26.1 g of 3,3;17,17-bis[1,2-ethanediylbis (oxy)]estr-5-en-11 -one is dissolved in 350 ml of absolute methylene chloride and mixed under protective gas with 18 ml of 2,6-ditertiarybutylpyridine After cooling this solution to 0° C., 12.9 ml of trifluoromethanesulfonic acid anhydride is slowly instilled. Then the reaction mixture is stirred for 20 hours more at room temperature. For working up it is poured on saturated sodium bicarbonate solution, the organic phase is separated and the aqueous phase is reextracted with methylene chloride. The combined organic phases are washed with saturated sodium chloride solution, dried on sodium sulfate and concentrated by evaporation in a vacuum. After chromatography of the crude product on silica gel with a mixture of ethyl acetate/hexane, in addition to 16.4 ml of 2,6-ditertiary-butylpyridine and 5.1 g of 3,3;17,17-bis[1,2-ethanediylbis(oxy)]estr-5-en-11-one, 27 g of the title compound 1A is obtained as white foam.

$[\alpha]^{20}_D = +104°$ (CHCl$_3$; c=0.505)

$^1$H-NMR(CDCl$_3$) δ=5.58 dbr (J=5 Hz,1H,H-6); 3.7–4.0 m (8H, ketal); 2.88 dbr (J=11 Hz, 1H, H-10); 2.74 dtr (J=16, 2.5 Hz, 1H, H-12); 2.18–2.33 m (2H,H-4); 0.84 s (3H,H-18).

B) 3,3;17,17-Bis[1,2-ethanediylbis(oxy)]-11-(4 -methoxyphenyl)estra-5,9(11)-diene (1B)

27 g of 1A is dissolved in a mixture of 450 ml of absolute toluene and 210 ml of absolute ethanol and mixed in succession with 3.1 g of palladiumtetrakistriphenylphosphine, 4.5 g of lithium chloride, 70 ml of 2 molar sodium carbonate solution and 9 g of (4-methoxyphenyl)boronic acid. The reaction mixture is then stirred for 2 hours at 95° C. cooled to room temperature and mixed with saturated sodium chloride solution. The organic phase is separated, washed in succession with 5% sodium hydroxide solution and water, dried on sodium sulfate and concentrated by evaporation in a vacuum. The residue is chromatographed on silica gel with a mixture of ethyl acetate/hexane. 24 g of 1B is obtained as white foam.

C) 3,3;17,17-Bis[1,2-ethanediylbis(oxy)]-11β-(4-methoxyphenyl)estra- 5-ene (1C)

1000 ml of ammonia is condensed at −70° C. and mixed with 1,80 g of lithium. After occurrence of the characteristic blue coloration, 24 g of 1B dissolved in 500 ml of absolute tetrahydrofuran is instilled. After 20 minutes of stirring the excess lithium is decomposed by addition of water, the ammonia is evaporated, the reaction mixture is poured on saturated ammonium chloride solution and the aqueous phase is extracted with ethyl acetate. The combined organic phases are washed with sodium chloride solution, dried on sodium sulfate and concentrated by evaporation in a vacuum. After chromatography of the crude product on silica gel with a mixture of ethyl acetate/hexane, 19.6 g of title compound ! C. and 1.8 g of 3,3;17,17-bis[1,2-ethanediylbis(oxy)]- 11-(4-hydroxyphenyl)estra-5,9(11)-diene are isolated as white foams.

D) 3,3-[1,2-Ethanediylbis(oxy)-11β-(4-methoxyphenyl)estra- 5-en-17-one (1D)

59 g of silica gel is suspended in 130 ml of methylene chloride mixed with 5.9 ml of saturated oxalic acid and stirred for 15 minutes more. 19.6 g of 1C is added to this suspension and the reaction mixture is stirred for 4 more hours at room temperature. Then it is suctioned off on a frit, the frit residue is washed again with methanol/methylene chloride and the thus obtained filtrate is shaken out with saturated sodium bicarbonate solution. The organic phase is dried on sodium sulfate and concentrated by evaporation in a vacuum. The residue is chromatographed on silica gel with a mixture of ethyl acetate/hexane. 13.77 g of 1D is obtained white foam.

E) 3,3-[1,2-Ethanediylbis(oxy)]-11β-(4-methoxyphenyl)-5,6α-epoxy- 5α-estran-17-one (1E)

4.75 g of 1D is dissolved in 35 ml of methylene chloride. It is mixed with 3.8 ml of saturated sodium bicarbonate solution, cooled on 0° C. and 1.23 g of m-nitrotrifluoroacetophenone is added. Then 4.66 ml of a 30% hydrogen peroxide solution is instilled. It is stirred for 4 days more at room temperature. Then reaction mixture is carefully mixed at slight cooling with saturated sodium thiosulfate solution. It is extracted with methylene chloride, the organic phase is washed with 5% sodium hydroxide solution as well as with saturated sodium chloride solution and dried on sodium sulfate. It is concentrated by evaporation in a vacuum. The crude product is purified by column chromatography. 3.74 g of 1E is obtained.

$^1$H-NMR(CDCl$_3$) δ=7.24 d (J=10 Hz, 2H, At); 6.79 d (J=10 Hz, 2H, Ar); 3.72–4.02 m (4H, ketal); 3.80 s (3H, OMe); 3.25 ddbr (J=7.5 Hz, 1H, H-11); 2.97 d (J=5 Hz, 1H, H-6); 0.60 s (3H, H-18)

F) 3,3-[1,2-Ethanediylbis(oxy)]-11β-(4-methoxyphenyl)-5α-estra- 5,17β-diol (1F)

3.74 g of 1E is dissolved in 250 ml of absolute ethanol. 6.45 g of sodium borohydride is carefully added and it is refluxed for 1 hour. Then the reaction solution is poured on water. It is extracted with methylene chloride, the organic phase is washed with saturated sodium chloride solution, dried on sodium sulfate and concentrated by evaporation in a vacuum. 3.99 of 1F is obtained which is used as crude product in the next step.

$^1$H-NMR(CDCl$_3$) δ=7.29 d (J=10 Hz, 2H, At); 6.78 d (J=10 Hz, 2H, Ar); 3.85–3.97 m (4H, ketal); 3.70 s (3H, OMe); 3.58 ddbr (J=14.7 Hz, 1H, H-17); 3.12 m (1H, H-11); 0.47 s (3H, H-18)

G) 3,3-[1,2-Ethanediylbis(oxy)]-5-hydroxy-11β-(4-methoxyphenyl)- 5α-estran-17-one (1G)

2.36 g of chromium trioxide is added to 7.9 ml of pyridine in 30 ml of methylene chloride at 0° C. and it is allowed to stir for 30 minutes. Then a solution of 1.74 g of 1F in 6 ml of methylene chloride is instilled and stirred for 1 hour more at 0° C. The reaction solution is then washed with 5% sodium hydroxide solution, as well as saturated sodium chloride solution. It is dried on sodium sulfate and concentrated by evaporation in a vacuum. The crude product is purified by crystallization on diisopropyl ether. 1.21 g of title compound 1G is obtained.

$^1$H-NMR(CDCl$_3$) δ=7.29 d (10 Hz, 2H, Ar); 6.78 d (J=10 Hz, 2H, Ar); 3.85–4.00 m (4H, ketal); 3.78 s (3H, OMe); 3.18 m (1H, H-11); 0.58 s (3H, H-18)

H) 3,3-[1,2-Ethanediylbis(oxy)]-11β-(4-methoxyphenyl)-17 -[(trimethylsilyl)oxy]-5α-estr-16-en-5-ole (1H)

Lithium diisopropyl amine is produced in absolute tetrahydrofuran from 1.10 ml of diisopropyl amine and 4.8 ml of a 1.6 molar butyl lithium solution (in hexane) at −30° C. Then 1.21 g of 1G in 10 ml of absolute tetrahydrofuran is instilled at −40° C. and stirred for 1 hour. Then 1.04 ml of trimethylsilyl chloride is instilled. It is stirred for 30 minutes at room temperature, then the reaction mixture is poured on saturated sodium bicarbonate solution and extracted with ethyl acetate. The organic phase is washed with saturated ammonium chloride solution as well as saturated sodium chloride solution, dried on sodium sulfate and concentrated by evaporation. The thus obtained 1H is further used directly.

I) 17-Chloro-3,3-[1,2-ethanediylbis(oxy)]-5-hydroxy-11β-(4 -methoxyphenyl)-17a-homo-5α-estr-16-en-17a-one (1I)

To this end 1H is dissolved in a mixture of 2.5 ml of ethylene glycol dimethyl ether and 7.55 ml of tetrachloroethylene, mixed with 980 mg of sodium trichloroacetate and refluxed for 20 hours (after about 8 hours another 980 mg of sodium trichloroacetate is added). Then the reaction solution is poured on water. It is extracted with methylene chloride. The organic phase is washed with saturated ammonium chloride solution as well as saturated sodium chloride solution, dried on sodium sulfate and concentrated by evaporation in a vacuum. The crude product is purified by column chromatography on silica gel with a mixture of hexane/ethyl acetate. 800 mg of 1I is obtained.

$^1$H-NMR(CDCl$_3$) δ=7.31 d (J=10 Hz, 2H, Ar); 6.98 dd (J=6, 1.5 Hz, 1H, H-16); 6.79 d (J=10 Hz, 2H, Ar); 3.85–3.98 m (4H, ketal); 3.22 ddbr (J=7.5 Hz, 1H, H-11); 2.64 ddd (J=19, 5.5, 4.5 Hz, 1H, H-15); 2.38 dd (J=15, 1.5 Hz, 1H, H-12); 2.08 dd (J=19, 2.5 Hz, 1H, H-15α); 1.95 dd (J=15, 5.5, 1H, H-12); 0.73 s (3H, H-18)

K) 17-Chloro-3,3-[1,2-ethanediylbis(oxy)]-11β-(4 -methoxyphenyl)-17aα-(1-propinyl)-17a-homo-5-estr-16-ene-5, 17aβ-diol 1K)

Propine is directed over 40 minutes in 130 ml of absolute tetrahydrofuran at 0° C. The reaction flask is flushed with argon and then 10.3 ml of a 1.6 molar butyl lithium solution in hexane is instilled at −8° C. It is stirred for 30 minutes and then 800 mg of 1I, dissolved in 8.2 ml of THF, is instilled. It is stirred for 2 hours more at 0° C. Then 30 ml of saturated ammonium chloride solution is instilled. It is extracted with ethyl acetate, the organic phase is washed with saturated sodium chloride solution, dried on sodium sulfate and concentrated by evaporation in a vacuum. 781 mg of 1K is obtained. The crude product is used in the next stage without purification.

$^1$H-NMR(CDCl$_3$) δ=7.31 d (J=10 Hz, 2H, Ar); 6.78 d (J=10 Hz, 2H, Ar); 5.79 dd (J=5, 2.5 Hz, 1H, H-16); 3.86–4.00 m (4H, ketal); 3.80 s (3H, OMe); 3.22 ddbr (J=7.5 Hz, 1H, H-11); 2.53 dd (J=14, 6.5 Hz, 1H, H-15); 2.13 dd (J=14, 2.5 Hz, 1H, H-15); 1.93 s (3H, Me); 0.56 s (3H, H-18)

L) 17-Chloro-11β-(4-methoxyphenyl)-17aα-hydroxy-17aα-(1 -propinyl)-17a-homoestra-4,16-dien-3 -one (1L)

779 mg of 1K is dissolved in 26 ml of acetone. It is mixed with 1.95 ml of 2 molar aqueous hydrochloric acid and stirred for 2 hours at room temperature. Then the reaction solution is poured on saturated sodium bicarbonate solution and extracted with methylene chloride. The organic phase is washed with saturated sodium chloride solution, dried on sodium sulfate and concentrated by evaporation in a vacuum. The crude product is purified by column chromatography on silica gel with a mixture of hexane and ethyl acetate. 435 mg of title compound 1L is obtained as white foam.

$^1$H-NMR(CDCl$_3$) δ=7.35 d (J=10 Hz, 2H, Ar); 6.83 d (J=10 Hz, 2H, Ar); 5.86 sbr (1H, H-4); 5.80 dd (J=5, 1 Hz, 1H, H-16); 3.80 s (3H, OMe); 3.39 ddbr (J=7.5 Hz, 1H, H-11); 2.89 m (1H, H-10); 1.92 s (3H, Me); 0.68 s (3H, H-18)

$[α]^{20}_D$=−120° (CHCl$_3$; cc=0.510)

D =

EXAMPLE 2

Production of 17-chloro-17aβ-hydroxy-17aα-(1-propinyl)-11β -[4-(3-pyridinyl)phenyl]-17a-homoestra-4,16-dien-3-one A) 3,3-[1,2-Ethanediylbis(oxy)]-11β-(4-hydroxyphenyl)-5α -estra-5,17β-diol (2A)

2.41 g of 1F is dissolved in 25 ml of absolute dimethylformamide. It is mixed in argon counterstream with 1.53 g of sodium methanethiolate and refluxed for 2 hours. Then the reaction solution is poured on about 50 ml of ice water. It is extracted with ethyl acetate, the organic phase is washed with saturated sodium chloride solution, dried on sodium sulfate and concentrated by evaporation in a vacuum. The crude product is purified by column chromatography on silica gel with a mixture of hexane/ethyl acetate. 1.37 g of 2A is obtained as white foam.

$^1$H-NMR(CDCl$_3$) δ=7.23 d (J=10 HZ, 2H, Ar); 6.71 d (J=10 Hz, 2H, Ar); 3.85–3.97 m (4H, ketal); 3.58 dd (J=12.5 Hz, 1H, H-17); 3.12 m (1H, H-11); 0.46 s (3H, H-18)

B) 3,3-[1,2-Ethanediylbis(oxy)]-11β-[4 -[[(trifluoromethyl)sulfonyl]oxy]phenyl]-5α-estra-5,17β-diol (2B)

1.37 g of 2A is dissolved in 50 ml of absolute methylene chloride. It is mixed with 1.94 g of dimethylaminopyridine, cooled to −78° C. and 0.7 ml of trifluoromethanesulfonic acid anhydride is instilled. It is then allowed to stir for 2 hours at −78° C. and then poured on saturated sodium bicarbonate solution. It is stirred for 30 more minutes and extracted with methylene chloride. The organic phase is washed with saturated sodium chloride solution, dried on sodium sulfate and concentrated by evaporation in a vacuum. The crude product is purified by column chromatography on silica gel with a mixture of hexane and ethyl acetate. 1.14 g of 2.B is obtained as white foam.

$^1$H-NMR(CDCl$_3$) δ=7.48 d (J=10 Hz, 2H, At); 7.16 d (J=10 Hz, 2H, Ar); 3.84–3.97 m (4H, ketal); 3.58 dd (J=12.5, 5 Hz, 1H, H- 17); 3.21 ddbr (J=7.5 Hz, 1H, H-11); 0.41 s (3H, H-18)

C) 3,3-[1,2-Ethanediylbis(oxy)]-11β-[4 -[[(trifluoromethyl)sulfonyl]oxy]phenyl]-5α-estran-17-one (2C)

1.22 g of chromium trioxide is added to 4.07 ml of pyridine in 15 ml of methylene chloride and stirred for 15 minutes at 0° C. Then 1.14 g of 2B is instilled in 5 ml of methylene chloride. It is allowed to stir for another hour at 0° C. The reaction solution is then washed with 5% aqueous sodium hydroxide solution as well as with saturated sodium chloride solution, dried on sodium sulfate and concentrated by evaporation in a vacuum. The crude product is purified by column chromatography on silica gel with a mixture of hexane and ethyl acetate. 1.03 g of 2C is obtained.

$^1$H-NMR(CDCl$_3$) δ=7.48 d (J=10 Hz, 2H, Ar); 7.18 d (J=10 Hz, 2H, Ar); 3.85–3.98 m (4H, ketal); 3.28 ddbr (J=7.5 Hz, 1H, H-11); 0.54 s (3H, H-18)

D) 17-Chloro-3,3-[1,2-ethanediylbis(oxy)]-5-hydroxy-11β-[4 -[[(trifluoromethyl)sulfonyl]oxy]phenyl]-17a-homo-5α-estr-16-en- 17a-one (2D)

3,3-[1,2-Ethanediylbis(oxy)]-11β-[4-4-[[(trifluoromethyl)sulfonyl]oxy]phenyl]-17-[(trimethylsilyl)oxy] -5α-estr-16-en-5-ol is first produced from 0.78 ml of diisopropyl amine and 3.46 ml of a 1.6 molar solution of butyl lithium in hexane as well as 1.03 g of 2C analogously to example 1H). Then 387 mg of D is produced by refluxing with 660 mg of sodium trichloroacetate in a mixture of 1.9 ml ethylene glycol dimethyl ether and 5.2 ml of tetrachloroethylene.

$^1$H-NMR(CDCl$_3$) δ=7.51 d (J=10 Hz, 2H, Ar); 7.18 d (J=10 Hz, 2H, Ar); 7.01 dd (J=6.2 Hz, 1H, H-16); 3.85–4.00 m (4H, ketal); 3.31 ddbr (J=7.5 Hz, 1H, H-11); 2.66 ddd (J=19.6, 4.5 Hz, 1H, H- 15β); 2.39 dd (J=15, 1.5 Hz, 1H, H-12β); 2.12 dd (J=19, 2.5 Hz, 1H, H-15); 2.01 dd (J=15.6 Hz, 1H, H-12α)

E) 17-Chloro-3,3-[1,2-ethanediylbis[oxy]-17aα-(1-propinyl)- 11β-[4-[[(trifluoromethyl)sulfonyl]oxy]phenyl]-17a-homo-5α-estr- 16-ene-17aβ-diol (2E).

As described in example 1K), 408 mg of 2E is produced from 4 ml of a 1.6 molar solution of butyl lithium in hexane, 387 mg of 2D and propine in 25 ml of absolute tetrahydrofuran. The crude product is used again without purification.

$^1$H-NMR(CDCl$_3$) δ=7.49 d (J=10 Hz, 2H, Ar); 7.16 d (J=10 Hz, 2H, Ar); 5.38 dd (J=5, 2.5 Hz, 1H, H-16); 3.85–4.00 m (4H, ketal); 3.40 ddbr (J=7.5 Hz, 1H, H-11); 2.59 dd (J=14.6, Hz, 1H, H-15β); 2.16 dd (J=14, 2.5 Hz, 1.H, H-15α); 1.92 s (3H, Me); 0.54 s (3H, H-18)

Compound 2E can also be produced in the following ways:

AA) 3,3-[1,2-Ethanediylbis(oxy)]-11β-(4-hydroxyphenyl)ester- 5-en-17-one (2AA)

Analogously to example 2A) 20 g of 1D and 13.4 g of sodium methanethiolate are reacted in 350 ml of dimethyl formamide. After completion of the reaction it is poured on 600 ml of ice water and stirred overnight. It is suctioned off and the filtrate is washed several times with water. 19 g of 2AA is obtained that is used in the following stage without purification.

AB) 11β-[4-[[Dimethyl(1,1-dimethylethyl)silyl]oxy]phenyl]-3,3 [1,2-ethanediylbis(oxy)]estr-5-en-17-one (2AB)

8.9 g of 2AA is dissolved in 90 ml of dimethylformamide. 4.63 g of 1H-imidazole and 4.93 g of dimethyl(1,1-dimethylethyl)silylchloride are added and stirred for 4 hours at room temperature. Then the reaction solution is poured on ice water and extracted with ethyl acetate. The organic phase is washed with saturated aqueous sodium chloride solution, filtered and concentrated by evaporation in a vacuum. The obtained crude product is purified by column chromatography on silica gel with a mixture of hexane/ethyl acetate. 10.27 g of 2AB is obtained as white foam.

$^1$H-NMR(CDCl$_3$) δ=7.09 d (J=8 Hz, 2H, Ar); 6.63 d (J=8 Hz, 2H, Ar); 5.46–5.48 m (1H, H-6); 3.80–3.90 m (4H, ketal); 3.30 ddbr (J=5, 7 Hz, 1H, H-11); 0.88 s (9H, t-Bu); 0.50 s (3H, C-18); 0.10 s (6H, SiMe$_2$)

AC) 11β-[4-[[Dimethyl(1,1-dimethylethyl)silyl]oxy]phenyl]-3,3 [1,2-ethanediylbis(oxy)]-5,6α-epoxy-5α-estran-17-one (2AC)

As described in example 1E), 2.63 g of 2AB, 549 mg of 3-nitrotrifluoroacetophenone, 209 ml of 30% hydrogen peroxide and 1.7 ml of saturated aqueous sodium bicarbonate solution are reacted in 20 ml of dichloromethane. 1.9 g of 2AC is obtained as white foam after column chromatography on silica gel with a mixture of hexane/ethyl acetate.

$^1$H-NMR(CDCl$_3$) δ=7.19 d (J=8 Hz, 2H, Ar); 6.72 d (J=8 Hz, H, Ar); 3.80–4.00 m (4H, ketal); 3.22 ddbr (J=5, 7 Hz, 1H, H-11); 2.96 d (J=5 Hz, 1H, H-6); 0.96 s (9H, t-Bu); 0.60 s (3H, C-18); 0.20 s (6H, SiMe$_2$)

AD) 11β-[4-[[Dimethyl(1,1-dimethylethyl)silyl]oxy]phenyl]-3,3 [1,2-ethanediylbis(oxy)-5α-estra-,5,17β-diol (2AD)

3.85 g of 2AC, dissolved in 30 ml of absolute tetrahydrofuran, is added to 550 mg of lithium aluminum hydride in 20 ml of absolute tetrahydrofuran at 0° C. It is allowed to stir for 30 minutes more at 0° C. and then 5 ml of saturated aqueous ammonium chloride solution is carefully added. The precipitated precipitate is filtered off on Celite. The filtrate is diluted with ethyl acetate and washed with saturated aqueous sodium chloride solution. It is dried on sodium sulfate, filtered and concentrated by evaporation in a vacuum. 3.26 g of 2AD is obtained as white foam after column chromatography on silica gel with a mixture of hexane/ethyl acetate.

$^1$H-NMR(CDCl$_3$) δ=7.20 d (J=8 Hz, 2H, Ar); 6.70 d (J=8 Hz, 2H, Ar); 3.85–4.00 m (4H, ketal); 3.55 m (1H, H-17); 3.10 ddbr (J=5, 7 Hz, 1H, H-11); 0.98 s (9H, t-Bu); 0.48 s (3H, C-18); 0.18 s (6H, SiMe$_2$)

AE) 11β-[4-[[Dimethyl(1,1-dimethylethyl)silyl]oxy]phenyl]-3,3 [1,2-ethanediylbis(oxy)]5-hydroxy-5α-estran-17-one (2AE)

3.37 g of 2AD, 3.73 g of chromium trioxide and 1.24 ml of pyridine are reacted analogously to example 1G). 3.23 g of 2AE is obtained as white foam after column chromatography on silica gel with a mixture of hexane/ethyl acetate.

$^1$H-NMR(CDCl$_3$) δ=7.20 d (J=8 Hz, 2H, Ar); 6.70 d (J=8 Hz, 2H, Ar); 3.85–3.95 m (4H, ketal); 3.15 ddbr (J=5, 7 Hz, 1H, H-11); 0.95 s (9H, t-Bu); 0.57 s (3H, C-18); 0.15 s (6H, SiMe$_2$)

AF) 11β-[4-[[Dimethyl(1,1-dimethylethyl)silyl]oxy]phenyl] -3,3 [1,2-ethanediylbis(oxy)]-17-[(trimethylsilyl)oxy]-5α-estr-16 -en-5-ol (2AF)

1.16 g of 2AF is produced in 60 ml of absolute tetrahydrofuran from 1.08 g of 2AE, 0.7 ml of diisopropylamine, 3.13 ml of a 1.6 molar solution of butyl lithium in hexane as well as 0.7 ml of trimethylsilyl chloride analogously to example 1H), which is used in the following stage without purification.

AG) 17-Chloro-11β-[4-[[Dimethyl(1,1-dimethylethyl)silyl]oxy]phenyl]-3,3 [1,2-ethanediylbis(oxy)]-5-hydroxy-17α-homo-5α-estr-16-en-17a-one (2AG)

1.16 g of 2AF is dissolved in 10 ml of trichloromethane. It is mixed with 10 mg of benzyltriethylammonium chloride as well as 2.1 g of sodium chloroacetate and refluxed for 3 hours. Then the reaction mixture is poured on water. It is extracted with dichloromethane, the organic phase is washed with saturated ammonium chloride solution as well as saturated aqueous sodium chloride solution, dried on sodium sulfate, filtered and concentrated by evaporation in a vacuum. 694 mg of 2AG is obtained as white foam after column chromatography on silica gel with a mixture of hexane/ethyl acetate.

$^1$H-NMR(CDCl$_3$) δ=7.25 d (J=8 Hz, 2H, Ar); 6.98 d (J=6, 1.5 Hz, 1H, H-16); 6.73 d (J=8 Hz, 2H, Ar); 3.90–4.00 m (4H, ketal); 3.20 ddbr (J=5, 7 Hz, 1H, H-11); 0.95 s (9H, t-Bu); 0.73 s (3H, C-18); 0.18 s (6H, SiMe$_2$)

AH) 17-Chloro-11β-[4-[[dimethyl(1,1dimethylethyl)silyl]oxy]phenyl]-3,3-[1,2-ethanediylbis(oxy)] -17aα-(1-propinyl) -17a-homo-5α-estr-16-en-17aβ-diol Analogously to example 1K), 694 mg of 2AG, 3.7 ml of a 1.6 molar solution of butyl lithium in hexane and propine gas are reacted in 30 ml of absolute tetrahydrofuran. 652 mg crude product of 2AH is obtained, which is used in the following stage without purification.

AI) 17-Chloro-3,3 [1,2-ethanediylbis(oxy)]-11β-(4-hydroxyphenyl-17aα-(1-propinyl)-17a-homo-5α-estr-16-ene-5,17aβ-diol (2AI)

652 mg of 2AH is dissolved in 10 ml absolute tetrahydrofuran. 820 of tetrabutylammonium fluoride-trihydrate is added and stirred for 1.5 hours more at room temperature. Then the reaction solution is poured on saturated aqueous sodium bicarbonate solution and extracted with ethyl acetate. The organic phase is washed with saturated sodium chloride solution, dried on sodium sulfate, filtered and concentrated by evaporation in a vacuum. 530 mg of 2AI is obtained which is used again without purification.

AK) 17-Chloro-3,3-[1,2-ethanediylbis(oxy)]-17aα-(1 propinyl)-11β-[4-[[(trifluoromethyl)sulfonyl]oxy]phenyl]-17a-homo- 5α-estr-16-ene-5,17aβ-diol (2E)

Analogously to example 2B) 530 mg of 2AI, 0.23 ml of trifluoromethanesulfonic acid anhydride and 0.74 g of 4-dimethylaminopyridine in 15 ml absolute dichloromethane are reacted. 504 mg of is obtained as white foam after column chromatography on silica gel with a mixture of hexane/ethyl acetate.

F) 17-Chloro-3,3-[1,2-ethanediylbis(oxy)]-17aα-(1-propinyl)-11β -[4-(3-pyridinyl)phenyl-17a-homo-5α-estr-16-ene-5,17aβ-diol (2F)

1.28 g of 2E is dissolved in 18 ml of toluene and 8 ml of ethanol. 408 mg of diethyl(3-pyridinyl)borane, 235 mg of tetrakis(triphenylphosphine)palladium, 170 mg of lithium chloride as well as 2.6 ml of a 2 molar aqueous sodium carbonate solution are added under argon and refluxed 1.5 hours. Then the reaction solution is poured on water and extracted with ethyl acetate. The organic phase is washed with saturated aqueous sodium chloride solution, dried on sodium sulfate and concentrated by evaporation in a vacuum. The crude product is chromatographed on silica gel with a mixture of ethyl acetate/hexane. 925 mg of 2F is obtained as white foam.

$^1$H-NMR(CDCl$_3$) δ=8.87 sbr (1H,Py); 8.56 dbr (J=4.5 Hz, 1H, Py); 7.90 dtr (J=7.5, 1 Hz, 1H, Py); 7.45–7.55 m (4H, Ar); 7.35 dd (J=7.5, 4.5 Hz, 1H, Py); 5.80 dd (J=5, 2.5 Hz, 1H, H-16); 3.90–4.00 m (4H, ketal); 3.30 ddbr (J=5.7 Hz, 1H, H-11); 1.96 s (3H, propine); 0.61 s (3H, C-18)

G) 17-Chloro-17aβ-hydroxy-17aα-(1-propinyl)-11β-[4-(3-pyridinyl)phenyl]-17a-homoestra-4,16-dien-3-one (2G)

Analogously to example 1L) 925 mg of F is reacted with 2 ml of normal aqueous hydrochloric acid in 25 ml of acetone. 619 of title compound 2G is obtained as white crystals after chromatography on silica gel with a mixture of hexane/ethyl acetate as well as recrystallization of diisopropyl ether.

$^1$H-NMR(CDCl$_3$) δ=8.87 sbr (1H,Py); 8.58 dbr (J=4.5 Hz, 1H, Py); 7.89 dtr (J=7.5, 1 Hz, 1H, Py); 7.37 dd (J=7.5, 4.5 Hz, 1H, Py); 7.58 d (J=10 Hz, 2H, Ar); 7.52 d (J=10 Hz, 2H, Ar); 5.88 sbr (1H, H-4); 5.80 dd (J=5, 2.5 Hz, 1H, H-16); 3.51 ddbr (J=7.5 Hz, 1H, H-11); 2.36 m (1H, H-10); 1.93 s (3H, Me); 0.68 s (3H, H-18)

$[\alpha]^{20}_D$=−67.4° (CHCl$_3$; c=0.525)

Melting point=195° C.

EXAMPLE 3

Production of 11β-(4-acetylphenyl)-17-chloro-17aβ-hydroxy- 17aα-(1-propinyl)-17a-homoestra-4,16-dien-3-one (3B)

A) 17-Chloro-3,3-[1,2-ethanediylbis(oxy)]-11β-[4-(1-ethoxyethenyl)phenyl]-17aα-(1propinyl)-17a-homo-5α-estr-16-ene- 5,17aβ-diol (3A)

500 mg of 2is dissolved in 6 ml of dioxane. 45 mg of tetrakis (triphenylphosphine) palladium, 67 mg of lithium chloride as well as 0.09 ml of pyridine are added under argon and refluxed for 2 hours. Then the reaction solution is filtered on Celite, diluted with ethyl acetate, washed with saturated aqueous sodium chloride solution, dried on sodium sulfate, filtered and concentrated by evaporation in a vacuum. 435 mg of 3A is obtained as white foam. The crude product is used in the following stage without further purification.

B) 11β-(4-Acetylphenyl)-17-chloro-17aβ-hydroxy-17aα-(1-propinyl)-17a-homoestra-4,16-dien-3-one 435 mg of 3A and 1.1 ml of 2 normal aqueous hydrochloric acid are reacted in 30 ml of acetone analogously to example 1L). 275 mg of title compound 3B is obtained as white foam after column chromatography on silica gel with a mixture of hexane/ethyl acetate.

$^1$H-NMR(CDCl$_3$) δ=7.90 d (J=8 Hz, 2H, Ar); 7.53 d (J=8 Hz, 2H, Ar); 5.87 sbr (1H, H-4); 5.80 dd (J=5, 2.5 Hz, 1H, H-16); 3.50 ddbr (J=5, 7 Hz, 1H, H-11); 2.60 s (3H, acetyl); 1.90 s (3H, propine); 0.62 s (3H, C-18)

$[\alpha]^{20}_D$=−88.7° (CHCl$_3$; c=0.505)

EXAMPLE 4

Production of 17-chloro-11β-[4-(3-furanyl)phenyl]-17aβ -hydroxy-17aα-(1-propinyl)-17a-homoestra-4,16-dien-3-one (4B)

A) 17-Chloro-3,3-[1,2-ethanediylbis(oxy)]-11β-[4-(3-furanyl)phenyl]-17aα-(1-propinyl)-17a-homo-5α-estr-16-ene-5,17aβ -diol (4A)

As described in example 3A), 1.76 g of 2E, 1.58 g of (3-furanyl)tributylstannane (production see Synthesis 898 (1985)), 155 mg of tetrakis(triphenylphosphine)palladium, 231 mg of lithium chloride as well as 0.29 ml of pyridine in 21 ml of dioxane are reacted. 1.23 g of 4A is obtained as white foam after column chromatography on silica gel with a mixture of hexane/ethyl acetate.

$^1$H-NMR(CDCl$_3$) δ=7.72 dbr (J=1.3 Hz, 1H, Fu-2); 7.45–7.50 m (3H, Ar+Fu-5); 6.70 dbr (J=1.8 Hz, 1H, Fu-4); 5.79 dd (J=5, 2.5 Hz, 1H, H-16); 3.90–4.00 m (4H, ketal); 3.29 ddbr (J=5, 7 Hz, 1H, H-11); 1.94 s (3H, propine); 0.62 s (3H, C-18)

B) 17-Chloro-11β-[4-(3-furanyl)phenyl]-17aβ-hydroxy-17aα-(1-propinyl)-17a-homoestra-4,16-dien-3-one (4B)

As described in example 1L), 1.23 g of 4A and 2.8 ml of 2 molar aqueous hydrochloric acid in 95 ml of acetone are reacted. 820 mg of title compound 4B is obtained as white foam after column chromatography on silica gel with a mixture of hexane/ethyl acetate.

H-NMR(CDCl$_3$) δ=7.72 dbr (J=1.3 Hz, 1H, Fu-2); 7.47 dd (J=1.8, 1.3 Hz, 1H, Fu-5); 7.38–7.45 m (4H, Ar); 6.70 dbr (J=1.8 Hz, 1H, Fu-4); 5.87 sbr (1H, H-4); 5.80 dd (J=5, 2.5 Hz, 1H, H-16); 3.44 ddbr (J=5, 7 Hz, 1H, H-11); 1.93 s (3H, propine); 0.70 s (3H, C-18)

Melting point: 158.5° C. (decomposition)

[α]$^{20}_D$=−67.8° (CHCl$_3$; c=0.510)

EXAMPLE 5

Production of 17-chloro-11β-[4-(3-furanyl)phenyl]-17aβ-hydroxy-17aα-methyl-17a-homoestra-4,16-dien-3-one (5C)

A) 17-Chloro-3,3-[1,2ethanediylbis(oxy)]-17aα-methyl-11β-[4-[[(trifluoromethyl)sulfonyl]oxy]phenyl-17a-homo-5α-estr-16-ene-5,17a-diol (5A)

3.6 ml of a 1.6 molar solution of methyl lithium in diethyl ether is mixed with 5 ml of absolute tetrahydrofuran. The solution is cooled to 0° C. and 687 mg of the compound produced in example 2D), dissolved in 6 ml of absolute tetrahydrofuran, is instilled. It is stirred for one hour at 0° C., the reaction solution is then poured carefully on water and extracted with ethyl acetate. The organic phase is washed with saturated aqueous sodium chloride solution, dried on sodium sulfate, filtered and concentrated by evaporation in a vacuum. The crude product is purified by column chromatography on silica gel with a mixture of hexane/ethyl acetate. 604 mg of 5A is obtained as white foam.

$^1$H-NMR(CDCl$_3$) δ=7.50 d (J=8 Hz, 2H, Ar); 7.18 d (J=8 Hz, 2H, Ar); 5.77 dd (J=5, 2.5 Hz, 1H, H-16); 3.90–4.00 m (4H, ketal); 3.30 ddbr (J=5, 7 Hz, 1H, H-11); 1.30 s (3H, C-20); 0.58 s (3H, C-18)

B) 17-chloro-3,3-[1,2-ethanediylbis(oxy)]-11β-[4-(3-furanyl)phenyl]-17aα-methyl-17a-homo-5-estr-16-ene-5,17a-diol (5B)

Analogously to example 3A), 604 mg of 5A, 414 mg of (3-furanyl)tributylstannane, 41 mg of tetrakis (triphenylphosphine) palladium, 61 mg of lithium chloride as well as 0.08 ml of pyridine in 10 ml of dioxane are reacted. 363 mg of 5B is obtained as white foam after column chromatography on silica gel with a mixture of hexane/ethyl acetate.

$^1$H-NMR(CDCl$_3$) δ=7.72 dbr (J=1.3 Hz, 1H, Fu-2); 7.48 dd (J=1.8, 1.3 Hz, 1H, Fu-5); 7.42 d (J=8, Hz, 2H, At); 7.39 d (J=8, Hz, 2H, Ar); 6.70 dbr (J=1.8 Hz, 1H, Fu-4); 5.73 dd (J=5, 2.5 Hz, 1H, H-16); 3.90–4.00 m (4H, ketal); 3.28 ddbr (J=7, 5 Hz, 1H, H-11); 1.31 s (3H, C-20); 0.62 s (3H, C-18)

C) 17-Chloro-11β-[4-(3-furanyl)phenyl]-17aβ-hydroxy-17aαmethyl-17a-homoestra-4,16-dien-3-one (5C)

As described in example 1L), 363 mg of 5B and 0.88 ml of 2 normal aqueous hydrochloric acid are reacted in 35 ml of acetone. 240 mg of title compound 5C is obtained as white crystals after column chromatography and recrystallization from diisopropyl ether.

$^1$H-NMR(CDCl$_3$) δ=7.73 dbr (J=1.3 Hz, 1H, Fu-2); 7.49 dd (J=1.8, 1.3 Hz, 1H, Fu-5); 7.45 d (J=8, Hz, 2H, Ar); 7.40 d (J=8 Hz, 2H, Ar); 6.70 dbr (J=1.8 Hz, 1H, Fu-4); 5.89 sbr (1H, H-4); 5.78 dd (J=5, 2.5 Hz, 1H, H-16); 3.45 ddbr (J=5, 7 Hz, 1H, H-11); 1.33 s (3H, C-20); 0.71 s (3H, C-18)

Melting point: 221.3° C. (decomposition)

[α]$^{20}_D$=+106.0° (CHCl$_3$; c=0.530)

EXAMPLE 6

Production of 17aβ-hydroxy-11β-(4-methoxyphenyl)-17aα-(1-propinyl)-17a-homoestra-4,16-dien-3-one (6E)

A) 16β,17β-Dihydro-3,3-[1,2-ethanediylbis(oxy)]-11β-(4-methoxyphenyl)-17β-[(trimethylsilyl)oxy]-3'H-cyclopropa[16,17]-5α-estran-5-ol (6A)

Production of the zinc-silver pair: 2 g of zinc powder (activated with 2 molar hydrochloric acid) is added to a solution of 12 mg silver(I)acetate in 12 ml of glacial acetic acid at 100° C. It is stirred for 30 seconds at 100° C., the glacial acetic acid is decanted and the resulting solid is washed once with glacial acetic acid as well as five times with absolute diethyl ether Then it is dried for six hours on a high vacuum.

Cyclopropanation: 655 mg of the zinc silver reagent is mixed with 2.5 ml of absolute diethyl ether. Then 0.64 ml of diiodomethane is added and heated lightly in an oil bath until an exothermic reaction is observed. The heat source is removed and a light refluxing is observed without further heating being supplied. It is allowed to continue stirring until no more reaction can be deflected (about 25 minutes), then dilution with 8.5 ml of absolute diethyl ether takes place and stirring is allowed to continue for another 30 minutes. Then 513 mg of dissolved in 5 ml of absolute diethyl ether is added. It is refluxed for 30 minutes, the mixture is allowed to come to room temperature, 0.93 ml of pyridine is added, it is filtered on Celite and concentrated by evaporation in a vacuum. The resulting crude product is purified by column chromatography on silica gel with a mixture of hexane/ethyl acetate. 211 mg of 6A is obtained as white foam.

$^1$H-NMR(CDCl$_3$) δ=7.28 d (J=8 Hz, 2H, Ar); 6.79 d (J=8 Hz, 2H, Ar); 3.90–4.00 m (4H, ketal); 3.80 s (3H, OMe); 3.18 ddbr (J=5, 7 Hz, 1H, H-11); 1.00 m (1H, three-membered ring); 0.85 m (1H, three-membered ring); 0.74 s (3H, C-18); 0.70 m (1H, three-membered ring); 0.10 m (9H, SiMe$_3$)

B) 16ξ-Chloro-3,3-[1,2-ethanediylbis(oxy)]-5-hydroxy-11β-(4-methoxyphenyl)-17a-homo-5α-estran-17a-one (6B)

788 mg of anhydrous iron(III)chloride is added to 2.8 ml of absolute dimethylformamide under argon at 0° C. Then a solution of 406 mg of 6A is instilled in 6 ml of dichloromethane and 0.4 ml of pyridine and allowed to stir for 3 hours in which the temperature slowly rises to room temperature. Then the reaction mixture is poured on saturated aqueous sodium bicarbonate solution. It is extracted with ethyl acetate, the organic phase washed with saturated aqueous ammonium chloride solution as well as saturated sodium chloride solution, dried on sodium sulfate, filtered and concentrated by evaporation in a vacuum. 370 mg of 6B is obtained. The crude product is used in the following stage without purification.

C) 3,3-[1,2-Ethanediylbis(oxy)]-5-hydroxy-11β-(4-methoxyphenyl)-17a-homo-5α-estr-16-en-17a-one (6C)

A mixture of 370 mg of 6B and 1.26 g of sodium acetate in 9 ml of ethanol is refluxed for 3 hours. Then the reaction mixture is diluted with ethyl acetate, washed with saturated aqueous sodium chloride solution, dried on sodium sulfate, filtered and concentrated by evaporation in a vacuum. 244 mg of is obtained as white foam after column chromatography on silica gel with a mixture of hexane/ethyl acetate.

$^1$H-NMR(CDCl$_3$) δ=7.28–7.35 m (3H,H-16+Ar); 6.77 d (J=8 Hz, 2H, Ar); 5.82 ddd (J=10, 1, 1 Hz, 1H, H-17); 3.90–4.00 m (4H, ketal); 3.80 s (3H, OMe); 3.56 ddbr (J=5, 7 Hz, 1H, H-11); 0.49 s (3H, C-18)

D) 3,3-[1,2-Ethanediylbis(oxy)]-5-hydroxy-11β-(4-methoxyphenyl)-17aα-(1-propinyl)-17a-homo-5-estr-16ene5,17aβ-diol (6D)

Analogously to example 1K), 212 mg of 6D is obtained as white foam from 244 mg of 6C, 2.98 ml of a 1.6 molar solution of butyl lithium and propine gas in 15 ml of absolute tetrahydrofuran after column chromatography on silica gel with a mixture of hexane/ethyl acetate.

$^1$H-NMR(CDCl$_3$) δ=7.31 d (J=8 Hz, 2H, Ar); 6.78 d (J=8 Hz, 2H, At); 5.63 ddd (J=10, 1, 1 Hz, 1H, H-16); 5.50 dbr (J=10 Hz, 1H, H-17); 3.90–4.00 m (4H, ketal); 3.80 s (3H, OMe); 3.22 ddbr (J=5, 7 Hz, 1H, H-11); 1.92 s (3H, propine); 0.57 s (3H, C-18)

E) 17aβ-Hydroxy-11β-(4-methoxyphenyl)-17aα-(1-propinyl)-17a-homoestra- 4,16-dien-3-one (6E)

As described in example 1L), 120 mg of title compound 6E is obtained as white foam from 212 mg of 6D and 0.5 ml of 2 normal aqueous hydrochloric acid in 9 ml of acetone after column chromatography on silica gel with a mixture of hexane/ethyl acetate.

$^1$H-NMR(CDCl$_3$) δ=7.37 d (J=8 Hz, 2H, Ar); 6.82 d (J=8 Hz, 2H, Ar); 5.87 sbr (1H, H-4); 5.67 ddd (J=10, 1, 1 Hz, 1H, H-16); 5.52 dbr (J=10 Hz, 1H, H-17); 3.80 s (3H, OMe); 3.40 ddbr (J=5, 7 Hz, 1H, H-11); 1.92 s (3H, propine); 0.64 s (3H, C-18)

EXAMPLE 7

Production of 17aβ-hydroxy-11β-(4-methoxyphenyl)-17aα -methyl-17a-homoestra-4,16-dien-3-one (7C)

A) 17-Chloro-3,3-[1,2-ethanediylbis(oxy)]-11β-(4-methoxyphenyl)-17 aα-methyl-17a-homo-5α-estra-5,17aβ-diol (7A)

Analogously to example 5A), 490 mg of 1I and 3.15 ml of a 1.6 molar solution of methyl lithium in diethyl ether are reacted in 18 ml of absolute tetrahydrofuran. 405 mg of 7A is obtained as white foam after column chromatography on silica gel with a mixture of hexane/ethyl acetate.

$^1$H-NMR(CDCl$_3$) δ=7.31 d (J=8 Hz, 2H, Ar); 6.79 d (J=8 Hz, H, Ar); 5.75 dd (J=5, 1 Hz, 1H, H-16); 3.90–4.00 m (4H, ketal); 3.80 s (3H, OMe); 3.21 ddbr (J=5, 7 Hz, 1H, H-11); 1.31 s (3H, C-20); 0.61 s (3H, C-18)

B) 3,3-[1,2-Ethanediylbis(oxy)]-11β-(4-methoxyphenyl)-17aα-methyl-17a-homo-5α-estr-16ene-5,17aβ-diol (7B)

20 mg of lithium is added to 7 ml of ammonia at −78° C. After the characteristic blue coloration occurs, 404 mg of 7A, dissolved in 4 ml of absolute tetrahydrofuran, is rapidly added, and a decolorization of the reaction mixture is observed. As soon as a blue coloration is again observed, water is carefully added and the ammonia can escape. Then it is extracted with ethyl acetate. The organic phase is washed with saturated aqueous ammonium chloride solution as well as saturated aqueous sodium chloride solution, dried on sodium sulfate, filtered and concentrated by evaporation in a vacuum. The crude product is purified by column chromatography on silica gel with a mixture of hexane/ethyl acetate. 347 mg of 73 is obtained as white foam.

$^1$H-NMR(CDCl$_3$) δ=7.32 d (J=8 Hz, 2H, Ar); 6.28 d (J=8 Hz, 2H, Ar); 5.55 ddd (J=10, 1, 1 Hz, 1H, H-16); 5.34 dbr (J=10 Hz, 1H, H-17); 3.90–4.00 m (4H, ketal); 3.80 s (3H, OMe); 3.21 ddbr (J=5, 7 Hz, 1H, H-11); 1.25 s (3H, C-20); 0.59 s (3H, C-18)

C) 17aβ-hydroxy-11β-(4-methoxyphenyl-17aα-methyl-17a -homoestra-4,16-dien-3-one (7C)

As described in example 1L) 226 mg of title compound 7C is obtained as white foam from 347 mg of 7B and 1 ml of 2 normal aqueous hydrochloric acid in 20 ml of acetone after column chromatography on silica gel with a mixture of hexane/ethyl acetate.

$^1$H-NMR(CDCl$_3$) δ=7.36 d (J=8 Hz, 2H, Ar); 6.82 d (J=8 Hz, 2H, Ar); 5.86 sbr (1H, H-4); 5.58 ddd (J=10, 1, 1 Hz, 1H, H-16); 5.39 dbr (J=10 Hz, 1H, H-17); 3.80 s (3H, OMe); 3.45 ddbr (J=5, 7 Hz, 1H, H-11); 1.25 s (3H, C-20); 0.66 s (3H, C-18)

EXAMPLE 8

Production of 17aβ-hydroxy-11β-(4-methoxyphenyl)-17aα-(1 -propinyl)-17a-homoestr-4-en-3-one (8C)

A) 3,3-[1,2-Ethanediylbis(oxy)]-5-hydroxy-11β-(4-methoxyphenyl)-17a-homo-5α-estran-17-one (8A)

244 mg of 1I, 5 mg of azoisobutyronitrile and 0.4 ml of tributyltinhydride are refluxed in 20 ml of absolute toluene for 1.5 hours. After cooling it is concentrated by evaporation in a vacuum and the residue is purified by column chromatography on silica gel with a mixture of hexane/ethyl acetate. 160 mg of 8A is obtained as white foam.

$^1$H-NMR(CDCl$_3$) δ=7.31 d (J=8 Hz, 2H, Ar); 6.29 d (J=8 Hz, 2H, Ar); 3,90–4.00 m (4H, ketal); 3.79 s (3H, OMe); 3.20 ddbr (J=5, 7 Hz, 1H, H-11); 0.80 s (3H, C-18)

B) 3,3-[1,2-Ethanediylbis(oxy)]-11β-(4-methoxyphenyl)-17aα-(1-propinyl)-17a-homo-5α-estra-5,17aβ-diol (8B).

Analogously to example 1K), 246 mg of 8B is obtained as white foam from 338 mg 8A, 4.65 ml of a 1.6 molar solution of butyl lithium in hexane and propine gas in 20 ml of absolute tetrahydrofuran after column chromatography on silica gel with a mixture of hexane/ethyl acetate.

$^1$H-NMR(CDCl$_3$) δ=7.30 d (J=8 Hz, 2H, Ar); 6.29 d (J=8 Hz, 2H, Ar); 3,90–4.00 m (4H, ketal); 3.80 s (3H, OMe); 3.19 ddbr (J=5, 7 Hz, 1H, H-11); 1.93 s (2H, propine); 0.60 s (3H, C-18)

C) 17aβ-Hydroxy-11β-(4-methoxyphenyl)-17aα-(1-propinyl)-17 a-homoestr-4-en-3-one (8C)

Analogously to example 1L) 184 mg of title compound 8C is obtained as white foam from 246 mg of 8B and 0.6 ml of 2 normal aqueous hydrochloric acid in 10 ml of acetone after column chromatography on silica gel with a mixture of hexane/ethyl acetate.

$^1$H-NMR(CDCl$_3$) δ=7.33 d (J=8 Hz, 2H, Ar); 6.83 d (J=8 Hz, 2H, Ar); 5.85 sbr (1H, H-4); 3.80 s (3H, OMe); 3.35 ddbr (J=5, 7 Hz, 1H, H-11); 1.90 s (3H, propine); 0.67 s (3H, C-20)

TABLE 1

| Test compound | Dose mg/animal/day p.o. | Abortion rate n abort/n total | % |
|---|---|---|---|
| A | 3.0 s.c. | 4/4 | 100 |

TABLE 1-continued

| Test compound | Dose mg/animal/day p.o. | Abortion rate n abort/n total | % |
|---|---|---|---|
|  | 0.3 | 1/4 | 25 |
| B | 1.0 | 4/4 | 100 |
|  | 0.3 | 4/4 | 100 |
|  | 0.1 | 4/4 | 100 |
| C | 1.0 | 4/4 | 100 |
|  | 0.3 | 4/4 | 100 |
|  | 0.1 | 2/4 | 50 |

We claim:

1. A compound of formula I

[Structure of formula (I)]

wherein

X is an oxygen atom, the hydroxyimino grouping >N~OH or two hydrogen atoms, $R^1$ is a hydrogen atom or a methyl group, $R^2$ is an hydroxy group, a $C_1$–$C_{10}$ alkoxy or $C_1$–$C_{10}$ acyloxy group, $R^3$ is a hydrogen atom, the grouping —$(CH_2)_n CH_2 Z$, wherein n is 0, 1, 2, 3, 4 or 5, Z is a hydrogen atom, the cyano group or the radical —$OR^5$ wherein $R^5$ is H, $C_1$–$C_{10}$ alkyl or $C_1$–$C_{10}$ acyl, the grouping —$(CH_2)_m C \equiv C$—Y, wherein m is 0, 1 or 2 and Y is a hydrogen, fluorine, chlorine, bromine or iodine atom, a methyl, $C_1$–$C_{10}$ hydroxy alkyl, $C_1$–$C_{10}$ alkoxyalkyl, $C_1$–$C_{10}$ acyloxyalkyl radical, the grouping —$(CH_2)_p$—CH=CH—$(CH_2)_k CH_2 R^6$, wherein p is 0 or 1 and k is 0, 1 or 2 and $R^6$ is a hydrogen atom, a hydroxy group, a $C_1$–$C_4$ alkoxy or $C_1$–$C_4$ acyloxy radical, or else $R^2$ and $R^3$ together stand for a radical of the formula

[Three cyclic substructures shown]

in which x=1 or 2

$R^4$ is a hydrogen atom, a cyano group, a chlorine, fluorine, bromine, iodine atom, a trialkylsilyl group, trialkylstannyl group, a straight-chain or branched, saturated or unsaturated $C_1$–$C_8$ alkyl, $C_1$–$C_8$ acyl or alkoxyalkyl radical, an amino group N

[Structure with $R^7$, $R^8$]

wherein $R^7$ and $R^8$, independently of one another, are a hydrogen atom or a $C_1$–$C_4$ alkyl group, or a corresponding amine oxide

[Structure with N+, O-, $R^7$, $R^8$]

or the groupings —$OR^9$ or —$S(O)_i R^9$ wherein i is 0, 1 or 2, and $R^9$ is a hydrogen atom, a methyl, ethyl, propyl, isopropyl, methoxyphenyl, allyl or a 2-dimethylaminoethyl group, or a heteroaryl radical of the formula Iα

[Structure of formula (Iα) with A, B, D, E, $R^{10}$]

wherein

A is a nitrogen, oxygen or sulfur atom, —B—D—E— the element sequence —C—C—C—, —N—C—C— or —C—NC— and wherein $R^{10}$ is a hydrogen atom, a cyano group, a chlorine, fluorine, bromine or iodine atom, a trialkylsilyl, trialkylstannyl group, a straight-chain or branched, saturated or unsaturated $C_1$–$C_8$-alkyl, $C_1$–$C_8$-acyl or alkoxyalkyl radical, or an amino group N

[Structure with $R^7$, $R^8$]

wherein $R^7$ and $R^8$, independently of one another, are a hydrogen atom or a $C_1$–$C_4$ alkyl group, or a corresponding amine oxide

[Structure with N+, O-, $R^7$, $R^8$]

or the grouping —$OR^9$ or —$S(O)_i R^9$ wherein i is 0, 1 or 2, and $R^9$ is a hydrogen atom, a methyl, ethyl, propyl, isopropyl, methoxyphenyl, allyl or a 2-dimethylaminoethyl group, or a heteroaryl radical of formula Iβ

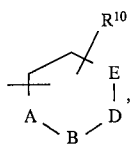
(Iβ)

wherein

A is a nitrogen atom and —B—D—E— means the element sequence —C—C—C—, —N—C—C—, —C—N—C— or —C—C—N— and $R^{10}$ has the meaning already indicated, or a phenyl radical of formula Iγ

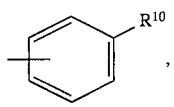
(Iγ)

wherein $R^{10}$ has the meaning already indicated, $R^{11}$ is fluorine, chlorine or bromine atom, and $R^{12}$ and $R^{13}$ together are an additional bond or $R^{11}$ is a straight-chain or branched-chain $C_1$-$C_4$-alkyl radical or a hydrogen atom, and $R^{12}$ and $R^{13}$ each are a hydrogen atom or together are an additional bond.

2. Compounds according to claim 1, namely

17aβ-Hydroxy-11β-(4-methoxyphenyl)-17aα-(1-propinyl)-17a-homoestra- 4,16-dien-3-one 17aβ-hydroxy-11β-(4-methoxyphenyl)-17aα-methyl-17a-homoestra- 4,16-dien-3-one 11β-[4-(3-furanyl)phenyl]-17aβ-hydroxy-17aα-(1-propinyl)- 17a-homoestra-4,16-dien-3-one 11β-(4-acetylphenyl)-17aβ-hydroxy-17aα-(1-propinyl)-17a-homoestra- 4,16-dien-3-one 17aβ-hydroxy-17aα-(3-hydroxypropyl)-11β-[4-(3-pyridinyl)phenyl]- 17a-homoestra-4,16-dien-3-one (Z)-4'-[17aβ-hydroxy-17aα-(3-hydroxy-1-propenyl)-3-oxo-17a-homo- 4,16-dien-11β-yl]-[1,1'-biphenyl]-4-carbonitrile 11β-[4-(3-furanyl)phenyl]-17aβ-hydroxy-17aα-methyl-17a-homoestra- 4,16-dien-3-one 11β-(4-acetylphenyl)-17aβ-hydroxy-17aα-(3-hydroxypropyl)-a-homoestra- 4-en-3-one 11β-(4-acetylphenyl)-4',5'-dihydrospiro[17a-homoestra-4-ene-17aβ,2' (3H)-furan]-3-one (Z)-4'-[17aβ-hydroxy-17aα-(3-hydroxy-1-propenyl)-3-oxo-17a-homoestr- 4-en-11β-yl]-[1,1'-biphenyl]-4-carbonitrile 17-chloro-11β-(4-methoxyphenyl)-17aβ-hydroxy-17aα-(1-propinyl)- 17a-homoestra-4,16-dien-3-one 17-chloro-17aβ-hydroxy-17aα-(1-propinyl)-11β-[4-(3-pyridinyl)phenyl]- 17a-homoestra-4,16-dien-3-one 11β-(4-acetylphenyl)-17-chloro-17aβ-hydroxy-17aα-(1-propinyl)- 17a-homoestra-4,16-dien-3-one 17-chloro-11β-[4-(3-furanyl)phenyl]-17aβ-hydroxy-17aα-(1-propinyl)- 17a-homoestra-4,16-dien-3-one 17-chloro-11β-[4-(3-furanyl)phenyl]-17aβ-hydroxy-17aα-methyl- 17a-homoestra-4,16-dien-3-one 4'-17-chloro-17aβ-hydroxy-17aα-methyl-3-oxo-17a-homoestra- 4,16-dien-11β-yl][1,1'-biphenyl]4-carbonitrile (Z)-11β-(4-acetylphenyl)-17-chloro-17aβ-hydroxy-17aα-(3-hydroxy- 1-propenyl)-17a-homoestra-4,16-dien-3-one 11β-(4-acetylphenyl)-17-chloro-17aβ-hydroxy-17aα-(3-hydroxypropyl)- 17a-homoestra-4,16-dien-3-one 17-chloro-11β-[4-(3-furanyl)phenyl]-17aβ-hydroxy-3-oxo-17a-homoestra- 4,16-dien-17aα-acetonitrile 11β-(4-acetylphenyl)-17-fluoro-17aβ-hydroxy-17aα-methyl-17a-homoestra- 4,16-dien-3-one 11β-(4-acetylphenyl)-17-fluoro-17aβ-hydroxy-17aα-(3-hydroxypropyl)- 17a-homoestra-4,16-dien-3-one 11β-(4-acetylphenyl)-17-fluoro-17aβ-hydroxy-17aα-(1-propinyl)- 17a-homoestra-4,16-dien-3-one 17aβ-hydroxy-11β-(4-methoxyphenyl)-17aα-(1-propinyl)-17a-homoestr- 4-en-3-one.

3. Intermediate products of general formula F

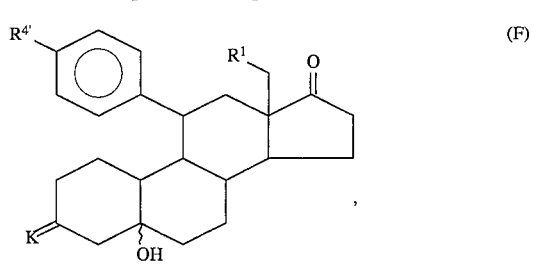
(F)

in which

K stands for the 1,2-ethanediylbis(oxy)-, 1,3-propanediylbis(oxy)-, 1,3-propane(2,2-dimethyl)-diylbis(oxy) groups or for another oxygen ketal $R^1$ stands for a hydrogen atom or a methyl group and $R^{4'}$ stands for a radical $R^4$ as already indicated in claim 1.

4. Pharmaceutical preparations containing at least one compound according to claim 1 as well as a pharmaceutical vehicle.

5. A method of preventing or terminating a pregnancy in a female in need of such treatment, comprising administering an effective amount of a compound of claim 1.

6. Process for the production of compounds of general formula I

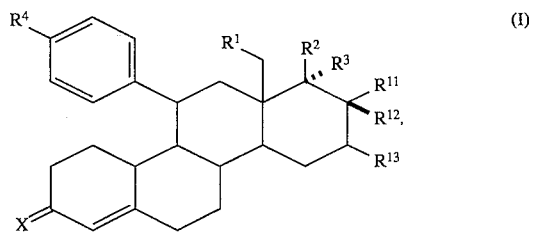
(I)

in which X $R^1$, $R^2$, $R^3$, $R^4$, $R^{11}$, $R^{12}$ and $R^{13}$ have the meaning indicated in claim 1, characterized in that a compound of general formula J or K

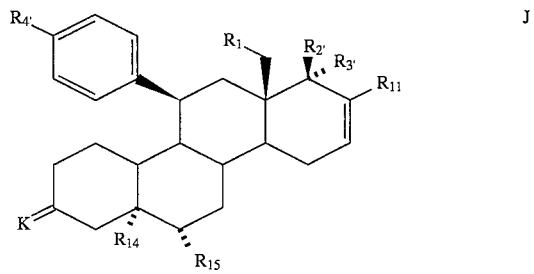
J

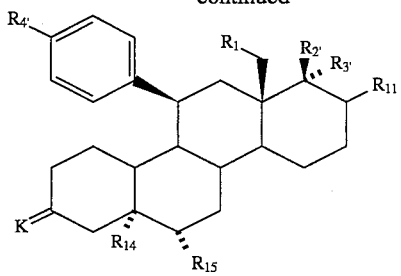

in which K is a keto group protected as ketal, $R^1$ and $R^{11}$ have the same meaning as in formula I as well as $R^{2'}$, $R^{3'}$ and $R^{4'}$ with the exclusion of the cyanide radical for $R^4$, have the same meaning as $R^2$, $R^3$ or $R^4$ in formula I, and existing hydroxy, mercapto, amino, oxo and/or terminal acetylene groups are optionally protected, and $R^{14}$ means an hydroxy group and $R^{15}$ means hydrogen, is subjected to the effect of an acid agent that is capable of freeing the 3-oxy group as well as the other protected groups and of dehydration with formation of the 4(5)-double bond, and then optionally hydroxy mercapto and/or amino group(s) present in $R^2$ and/or $R^3$ and/or $R^4$ is/are alkylated or acylated, optionally a cyanide radical is introduced in the 11β-aryl substituent, optionally the amino or sulfide group optionally contained in $R^4$ is oxidized, optionally reacted with hydroxylamine hydrochloride to the product of general formula I with X meaning the hydroxyimino group >N~H or the 3-oxo group is converted into a product of general formula I, in which X stands for 2 hydrogen atoms, and optionally a pharmaceutically compatible acid addition salt or salts is/are produced.

7. A compound of claim 1, wherein
$R^4$ is a hydrogen atom, a cyano group, a chlorine, fluorine, bromine, iodine atom, a trialkylsilyl group, trialkylstannyl group, a straight-chain or branched, saturated or unsaturated $C_1$–$C_8$-alkyl, $C_1$–$C_8$-acyl or alkoxyalkyl radical, an amino group N

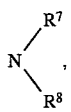

wherein $R^7$ and $R^8$, independently of one another, are a hydrogen atom or a $C_1$–$C_4$ alkyl group, or a corresponding amine oxide

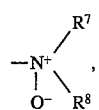

or the groupings —$OR^9$ or —$S(O)_iR^9$ wherein i is 0, 1 or 2, and $R^9$ is a hydrogen atom, a methyl, ethyl, propyl, isopropyl, methoxy-phenyl, allyl or a 2-dimethylaminoethyl group, or a pyridyl-$R^{10}$ group wherein $R^{10}$ is a hydrogen atom, a cyano group, a chlorine, fluorine, bromine or iodine atom, a trialkylsilyl, trialkylstannyl group, a straight-chain or branched, saturated or unsaturated $C_1$–$C_8$-alkyl, $C_1$–$C_8$-acyl or alkoxyalkyl radical, or an amino group

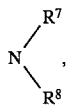

wherein $R^7$ and R, independently of one another, are a hydrogen atom or a $C_1$–$C_4$ alkyl group, or a corresponding amine oxide

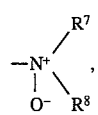

or the grouping —$OR$ or —$S(O)_iR^9$ wherein i is 0, 1 or 2, and $R^9$ is a hydrogen atom, a methyl, ethyl, propyl, isopropyl, methoxy-phenyl, allyl or a 2-dimethylaminoethyl group, or a phenyl radical of formula Iγ

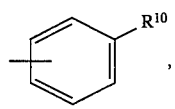

(Iγ)

wherein $R^{10}$ has the meaning already indicated.

* * * * *